United States Patent [19]

Zhu et al.

[11] Patent Number: 5,400,665
[45] Date of Patent: Mar. 28, 1995

[54] SAMPLE INTRODUCTION SYSTEM FOR INDUCTIVELY COUPLED PLASMA AND OTHER GAS-PHASE, OR PARTICLE, DETECTORS UTILIZING AN ENCLOSED FILTER SOLVENT REMOVAL SYSTEM, AND METHOD OF USE

[75] Inventors: Jianzhong Zhu; Daniel R. Wiederin; John E. Sutton, all of Omaha, Nebr.

[73] Assignee: Cetac Technologies Incorporated, Omaha, Nebr.

[21] Appl. No.: 25,665

[22] Filed: Mar. 3, 1993

Related U.S. Application Data

[63] Continuation-in-part of Ser. No. 766,049, Sep. 25, 1991, Pat. No. 5,259,254, Ser. No. 813,766, Dec. 27, 1991, Pat. No. 5,212,365, and Ser. No. 980,467, Nov. 23, 1992, Pat. No. 5,272,302.

[51] Int. Cl.$^6$ .............. G01N 1/28; H01J 49/26; B05B 1/02; B23K 9/00
[52] U.S. Cl. .............. 73/863.12; 73/864.81; 73/863.23; 250/288
[58] Field of Search .......... 73/863.11, 863.12, 863.23, 73/863.24, 863.25, 864.81, 864.85, 864.82, 864.83, 864.84, 864.86, 864.87; 250/288 R, 288 A; 261/78.2, DIG. 48; 239/102.2, 338, 341, 342, 343; 356/316; 219/121.48–121.52, 121.59; 315/111.21, 111.51, 111.71

[56] References Cited

U.S. PATENT DOCUMENTS

| | | | |
|---|---|---|---|
| 4,084,934 | 4/1978 | Kumazawa | 239/432 X |
| 4,206,160 | 6/1980 | Suddendorf et al. | 239/338 X |
| 4,985,529 | 9/1990 | Vestal | 73/864.81 |
| 5,192,865 | 3/1993 | Zhu | 250/288 |
| 5,212,365 | 5/1993 | Wiederin | 219/121.52 |
| 5,259,254 | 11/1993 | Zhu et al. | 73/864.81 |
| 5,272,308 | 12/1993 | Wiederin | 219/121.52 |

OTHER PUBLICATIONS

"Characterization of a Membrane Interface for Sample Introduction into Atom Reservoirs for Analytical Atomic Spectrometry" Spec Acta., vol. 43B, No. 8, pp. 917–922; published 1988 by Anders Gustavsson.

*Primary Examiner*—Thomas P. Noland
*Attorney, Agent, or Firm*—James D. Welch

[57] ABSTRACT

An efficient sample introduction system and method of use, for accepting liquid sample solutions, nebulizing them to form nebulized sample solution droplets, desolvating and removing solvent therefrom, and introducing the resulting desolvated nebulized sample particles to sample analysis systems is disclosed. In the preferred embodiment a flow of heated gas is caused to flow over the outer surface of a coiled essentially tubular shaped enclosed filter to remove solvent vapor which diffuses through the coiled essentially tubular shaped enclosed filter while a mixture of desolvated nebulized sample particles and solvent vapor is caused to flow therethrough. A modified embodiment utilizes a low temperature condenser in place of the heated gas flow. Nebulization of sample solutions is accomplished by use of high efficiency ultrasonic or direct injection micro nebulizer systems. Desolvation is performed in a desolvation chamber in which heating elements provide a temperature sufficient to vaporize solvent present. The sample introduction system provides improved sample solution nebulization, desolvation and solvent removal, as well as reduced sample loss and carry-over of sample from one analysis procedure to a subsequent analysis procedure, as compared to other systems which perform a similar overall function. The sample introduction system also enhances transport of sample through the sample introduction system to a sample analysis system. The present invention is equally effective with sample solutions in which the sample solvent is either water, or an organic solvent.

39 Claims, 6 Drawing Sheets

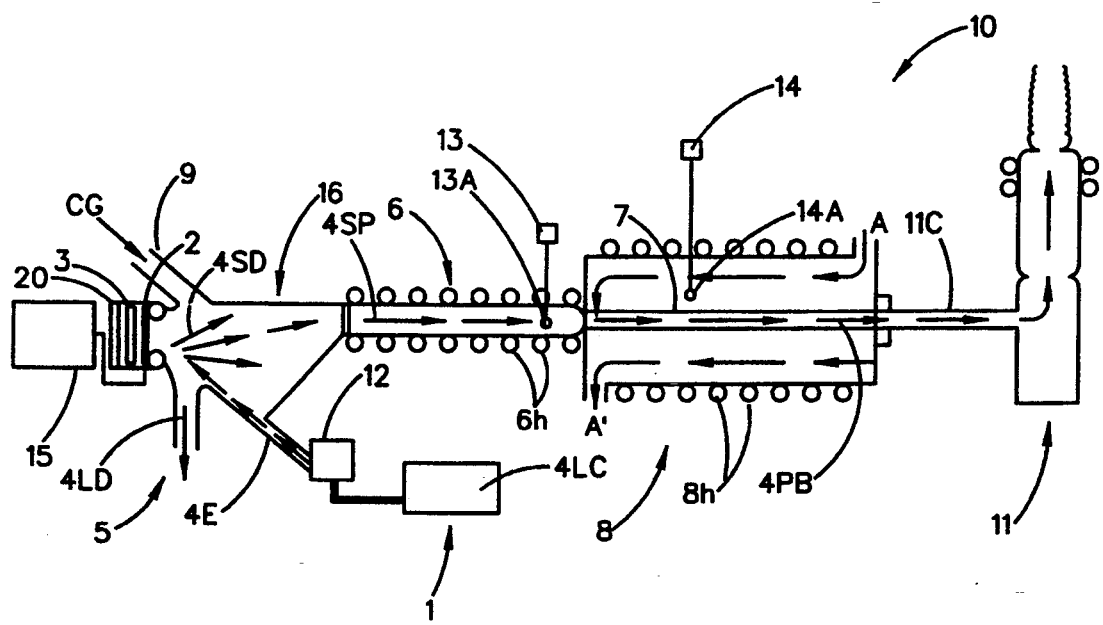
FIG. 1
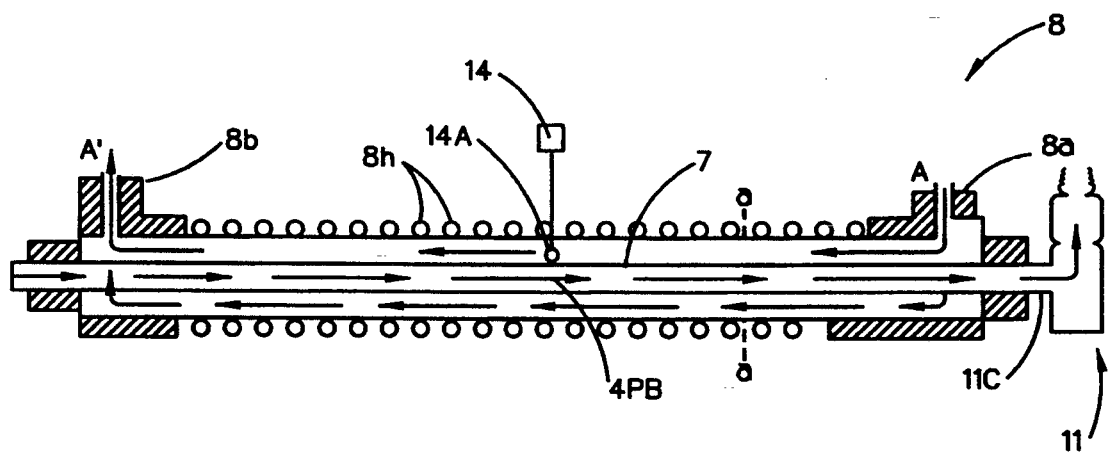
FIG. 2a
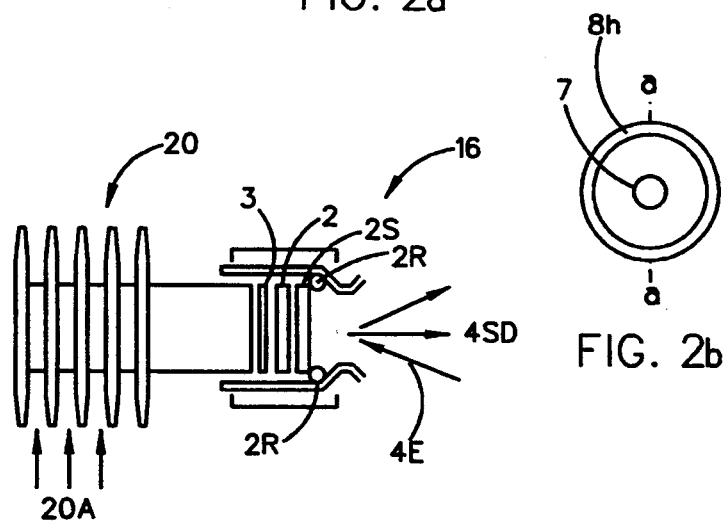
FIG. 2b
FIG. 3

SAMPLE INTRODUCTION SYSTEM FOR INDUCTIVELY COUPLED PLASMA AND OTHER GAS-PHASE, OR PARTICLE, DETECTORS UTILIZING AN ENCLOSED FILTER SOLVENT REMOVAL SYSTEM, AND METHOD OF USE

This application is a continuation-in-part of applications Ser. No. 07/766,049, filed Sep. 25, 1991, now U.S. Pat. No. 5,259,254, Ser. No. 07/813,766, filed Dec. 27, 1991, now U.S. Pat. No. 5,212,365, and Ser. No. 07/980,467, filed Nov. 23, 1992, now U.S. Pat. No. 5,272,302, all of which are assigned to CETAC Technologies Incorporated as common owner.

TECHNICAL FIELD

The present invention relates to a system and method of use for introducing liquid samples into gas-phase or particle detectors, such as inductively coupled plasma atomic emission spectrometers and mass spectrometers. More particularly, the present invention is directed to an enclosed filter solvent removal system used with ultrasonic, or total consumption direct injection micro nebulizer systems, to form a sample introduction system which provides both improved sample nebulization and long term system operational stability, both efficient sample desolvation and enhanced sample transport through the system, as well as reduced sample carryover from one analysis procedure to a subsequent analysis procedure.

BACKGROUND

The analysis of liquid samples by sample analysis systems which utilize gas-phase or particle detectors, such as inductively coupled plasma (ICP) atomic emission spectrometers, is well known. Typically, such sample analysis systems require that a sample solution first be nebulized into sample solution droplets. The sample solution droplets are then typically desolvated to form nebulized sample particles which are then transported to, and injected into, a detector element of the sample analysis system, wherein the nebulized sample particles are analyzed. In ICP and other plasma sample analysis systems for example, the nebulized sample particles are injected into a high temperature plasma where they interact with energy present in the plasma to form fragments such as molecules, atoms and/or ions. Electrons in the molecules, atoms and/or ions are excited to higher energy state orbitals by said interaction. When the electrons relax back into their lower energy, more stable state, orbitals, electromagnetic radiation is emitted. The frequence of the emitted electromagnetic radiation is a "fingerprint" of the contents of the sample and the intensity of the emitted electromagnetic radiation is related to the concentration of the components in the sample.

There are numerous existing systems for producing nebulized sample solution droplets, (which are typically desolvated to form nebulized sample particles), for introduction into gas-phase or particle sample analysis systems. These include pneumatic spray, thermospray, high pressure jet-impact, glass or metal frit, total consumption direct injection micro and ultrasonic nebulizer systems.

For decades pneumatic spray nebulizer systems were the most commonly used sample solution nebulizer systems for introduction of liquid samples into flame and plasma atomic spectrometry, (e.g. atomic emission, atomic absorbtion and atomic fluorescence) as well as mass spectrometers. Pneumatic nebulizers operate by introducing a sample solution through a small orifice into a concentrically flowing gas stream. Interaction between the sample solution and the concentrically flowing gas stream causes production of nebulized sample solution droplets. Pneumatic spray nebulizers, however, produce a wide spectrum of sample solution droplets, as regards the diameter thereof, and limited aerosol sample solution droplet per volume density. This is because relatively large diameter sample solution droplets typically leave the pneumatic nebulizer system under the influence of gravity. Sample analysis systems generally, it will be appreciated, operate with greater sensitivity and provide results which are more reproducable when large numbers of nebulized sample solution droplets are presented for analysis therein, which nebulized sample solution droplets are of a relatively constant and small, (e.g. 13 microns or less) diameter. This is because smaller droplets provide smaller desolvated sample particles which are more easily fragmented to produce molecules, atoms and/or ions. It is noted that the diameters of sample solution droplets formed by a pneumatic nebulization process are dependent on the concentrically flowing gas flow rate and on the size of the small orifice.

A more recently developed approach to nebulizing sample solutions involves use of thermospray nebulizers. Thermospray nebulizers control the temperature of the tip of a capillary tube such that solvent in a sample solution presented thereto, through said capillary tube, is caused to vaporize. The result of said solvent vaporization is formation of nebulized sample solution droplets. Thermospray nebulizers are typically used with mass spectrometer analysis systems as they operate best in low pressures, such as those present at the inlet stages of mass spectrometers. U.S. Pat. Nos. 4,883,958 and 4,958,529 and 4,730,111 to Vestal describe such nebulizing systems. It is noted that the diameters of sample solution droplets formed by the thermospray process are dependent upon the temperature of the capillary tube. It is also noted that the use of elevated temperatures can degrade sample analytes.

A Patent to Willoughby, U.S. Pat. No. 4,968,885 teaches a nebulizing system which uses both thermospray and pneumatic means. Sample solution droplet produced by the process of this nebulizing system have diameters which depend on both temperature and a gas flow rate.

A jet-impact nebulizing system is described by Doherty et al., (Appl. Spec. 38, 405–412, 1984). Said sample solution nebulizing system operates by forcing a sample solution through a nozzle which has an orifice therein on the order of twenty-five (25) to sixty (60) microns in diameter. The ejected sample solution impacts a wall and the interaction therewith causes formation of sample solution droplets. Again, sample solution droplet diameters depend on a flow rate as well as a driving pressure.

A glass frit nebulizer system is described by Layman, (Anal. Chem. 54, 638, 1982). A porous glass frit with numerous pores of a diameter from four (4) to eight (8) microns therethrough is positioned in the flow path of a sample solution. Sample solution which emerges therefrom is highly nebulized but the flow rate of the sample solution is typically low, (e.g. five (5) to fifty (50) microliters/min). While providing well nebulized sample solution droplets, this nebulizer system is prone to inconsistent sample solution flow rates, and must be subjected to repeated wash cycles between applications. It is noted that sample solution droplet diameters are dependent on a driving sample solution pressure.

The above presentation shows that the nebulizing systems surveyed present with various operational limitations. For instance, sample solution droplets produced by pneumatic, jet-impact and thermospray nebulizer systems, or combinations of thereof, have diameters which are dependent on gas flow rates or potentially sample degrading high temperatures. In addition, the glass frit nebulizers have inherent limitations as regards the amount of sample which they can nebulize and depend on a sample solution driving pressure to control sample solution droplet diameters. Said limited sample handling capability in these systems leads to a limit on the sensitivity of sample analysis systems which utilize them. A sample solution nebulizer system which would produce sample solution droplets with diameters determined by some independent variable other than a potentially sample analyte degrading elevated temperature, and which allows efficient sample volume flow handling capabilities would therefore be of utility. The identified attributes are associated with ultrasonic nebulizer systems, and with direct injection micro nebulizer systems.

Briefly, ultrasonic nebulizer systems generally provide means to impinge a sample solution onto, or in close proximity to a vibrating piezoelectric crystal or equivalent which is a part of an oscillator circuit. Typically the oscillator circuit system is calibrated so that radio frequency vibrations are produced. Interaction between the vibrational energy produced by the vibrating piezoelectric crystal or equivalent and the impinging sample solution causes the later to become nebulized into sample solution droplets as a result of the instability of the liquid-gas interface when exposed to a perpendicular force.

It is important to understand that the sample solution droplets produced by ultrasonic nebulizers have diameters which depend on the frequency of vibration of the piezoelectric crystal or equivalent, and that when the frequency of vibration is set to a megahertz level, a theoretically large number (e.g. seventy (70%) percent) of sample solution droplets can be formed with a relatively small uniform diameter of thirteen (13) microns or less. The important limitations of the sample solution nebulizer systems disclosed above are not present, (e.g. sample solution droplet diameters are not dependent on potentially sample analyte degrading elevated temperatures or any flow rates or pressures). Ultrasonic sample solution nebulizing systems are also capable of handling relatively high sample flows, and the sample solution droplet diameters produced by ultrasonic nebulizer system also tend to be more consistent than the diameters of sample solution droplets produced by other nebulizing systems. In addition, the conversion rate of sample solution to nebulized sample solution droplets is theoretically relatively high, being higher than ten (10%) to fifty (50%) percent as compared to approximately two (2%) percent when pneumatic nebulizer systems are used.

The presence of a far larger number and proportion of sample solution droplets with relatively small diameters means two things. First, less sample analyte is lost as a result of relatively large droplets falling away from entry to a detector element in a sample analysis system under the influence of gravity, hence, more sample analyte will be presented to said detector element; and second, the presence of smaller diameter sample solution droplets leads to production of smaller desolvated sample particles which are easier to fragment into molecules, atoms and/or ions for analysis. A larger amount of sample analyte is thus produced per fragmented sample particle. As a result, the sensitivity of a sample analysis system is improved when ultrasonic sample solution nebulizers are used, rather than other sample solution nebulizer systems.

A Patent to Olsen et al., U.S. Pat. No. 4,109,863 describes an ultrasonic nebulizer system in which a piezoelectric crystal or equivalent, (termed a transducer in Olsen et al.) is secured to the inner surface of a glass plate, which glass plate forms a leading portion of an enclosed hollow body, which hollow body is positioned in an aerosol chamber. The purpose of the glass plate is to provide the transducer protection against corrosion etc. which can result from contact with components in sample solutions. The glass plate is typically one-half (0.5) wavelengths of the transducer vibrational wavelength utilized, thick. This thickness optimizes effective transfer of vibrational energy therethrough. During use a sample solution is impinged upon the outer aspect of the glass plate, inside the aerosol chamber, rather than onto the transducer per se. The transducer is caused to vibrate and the interaction between the impinging sample solution and the vibrational energy produced causes production of nebulized sample solution droplets. In addition, a liquid coolant is circulated within the hollow body to maintain the transducer at a desired temperature. Problems which users of the Olsen et al. invention have experienced result from the use of a liquid to cool the transducer, and the use of a carrier gas injected from below the location of the transducer in the aerosol chamber. (It is noted that said carrier gas serves to sweep nebulized sample solution droplets toward a detector element in an analysis system). Even though the piezoelectric crystal is oriented vertically, bubbles tend to form on the back side of the transducer during use, resulting in uneven cooling of the transducer. This leads to reduced operational efficiency and lifetime of the transducer. In addition, the electrical leads to the transducer, from the other components of an oscillator circuit, pass through the cooling liquid,-and they tend to become corroded during use. Continuing, injecting a carrier gas into the aerosol chamber from a position below the location of the piezoelectric crystal or equivalent, as is done in the Olsen et al. ultrasonic nebulizer system, leads to pulsations in the volume density of the aerosol sample solution droplets which are produced over time which are available to sample analysis systems. In addition, the hollow body of the Olsen et al. invention is attached to the aerosol chamber thereof in a manner which creates "crevasses" therebetween. Sample from one analysis procedure can accumulate in the crevasses and by a "carry-over" capillary action or "wicking" effect be released and contaminate analysis results in subsequent analysis procedures. Continuing, the Olsen et al. invention directs nebulized sample solution droplet flow toward solvent vaporization, desolvation and sample analysis system detector elements by way of a relatively small diameter orifice. Turbulence results when the nebulized sample solution droplets pass through said relatively small diameter orifice and nebulized sample solution droplets are caused to reagglomerate, and are lost, as a result thereof. Finally, the hollow body construction of the Olsen et al. invention does not provide any vibrational energy focusing capability, since the vibrational energy produced by the transducer is emitted in all directions therefrom, without any means being present to redirect any of said vibrational energy.

A Patent to Dorn et al. U.S. Pat. No. 4,980,057 describes a sample solution nebulizer system which uses both ultrasonic and pneumatic means to nebulize sample solutions. A one-sixteenth (1/16) inch stainless steel tube is placed in the center of an ultrasonic nebulizer probe and serves to concentrate the vibrational energy produced by an ultrasonic transducer present therearound. A fused silica capillary tube is placed inside the one-sixteenth (1/16) inch stainless steel tube to, during use, deliver a high velocity gas stream to the tip of the ultrasonic nebulizer probe. Also during use, the sample solution is introduced to the surface of the ultrasonic nebulizer probe. Interaction between the sample solution, vibrational energy and high velocity gas stream causes the sample solution to be nebulized into sample solution droplets. It is noted that this system probably can not utilize megahertz level frequencies as the ultrasonic nebulizer probe is not of a small enough dimension, (e.g. on the order of half a wavelength of a megahertz vibrational frequency), to efficiently transmit megahertz wavelength vibrational energy waves to the location at which the sample solution is entered to the system. The Dorn et al. Patent teaches the use of one-hundred-and-twenty (120 KHZ) Kilohertz operational frequency. In addition, this system produces sample solution droplets, the diameters of which are affected by the flow rate of the sample solution nebulizing gas, as is the case with any pneumatic type sample solution nebulizing system.

A paper by Goulden et al., (Anal. Chem 56, 2327-2329, 1984) describes a modified ultrasonic nebulizer. The piezoelectric crystal or equivalent, termed a transducer in the Goulden paper, is oriented horizontally at the upper aspect of a glass container. A rubber stopper is placed below the transducer, inside the walls of the glass container. The rubber stopper has a vertically oriented centrally located hole therethrough such that a large amount of cooling water, (e.g. one-half (0.5) l/min) can be caused to flow vertically upward through said vertically oriented centrally located hole in the rubber stopper, into the space between the lower surface of the transducer and the upper surface of the rubber stopper, and out thereof around the edges of the rubber stopper and inside the glass container. The purpose of the described arrangement is to prevent bubbles from accumulating under the transducer during use, and thereby avoid instabilities of operation and reduced transducer lifetime.

A paper by Karnicky et al., (Anal. Chem., 59, 327-333, 1987) describes another design for an ultrasonic nebulizer. An enclosed chamber has, at a distance above the inside surface at of its lower extent, a piezoelectric crystal or equivalent, termed an ultrasonic transducer in the Karnicky paper, which ultrasonic transducer fits snuggly within the inner side walls of the enclosed chamber. Air is present between the upper surface of the lower extent of the enclosed chamber, and the lower surface of the ultrasonic transducer, but between the upper surface of the ultrasonic transducer and the lower surface of a glass diaphragm which is present at the upper aspect of the enclosed chamber, there exists a space through which cooling water is flowed during use. The ultrasonic transducer is shaped concave upward so that vibrational energy produced thereby during use is directed to and focused upon the glass diaphragm through the cooling water. An enclosed sample solution entry and carrier gas entry assembly mounts to the enclosed chamber above the location of the glass diaphram. During use the enclosed chamber with ultrasonic transducer therein, and with the enclosed sample solution and carrier gas entry assembly mounted thereto is oriented with its longitudinal axis at an approximate forty-five degree angle to an underlying horizontal surface. A sample solution is entered so that it impinges on the outer surface of the glass diaphragm at an approximate forty-five degree angle thereto. Interaction between vibrational energy produced by the ultrasonic transducer and the impinging sample solution produces nebulized sample solution droplets which are then transported to desolvation and solvent removal systems under the influence of a pressure gradient created by the entering of a carrier gas flow to the enclosed sample solution and carrier gas entry assembly. It is also noted that the Karnicky system provides a wick which contacts the outer surface of the glass diaphragm to drain away sample solution which is not nebulized during use.

Another paper, by Mermet et al., (Dev. Atomic Plasma Spec. Anal. Proc. Winter Conference, 245-250, 1980), describes yet another design for an ultrasonic nebulizer system. A piezoelectric crystal or equivalent, termed a transducer in the Mermet paper, is present within a waveguide structure which decreases in inner diameter along its upwardly projecting longitudinal axis, near the lower extent thereof. The internal waveguide structure is thus, conical in shape, and during use is filled with a vibrational energy transmitting bath. Said waveguide structure shape plays the role of an impedance transformer and use of low electrical power levels, (e.g. five (5) to seven (7) watts) to effect sample solution nebulization is made possibly, thereby reducing transducer cooling requirements. At the upper extent of said waveguide structure is present a nebulization cell, the lower extent of which is made from a thin membrane of ethylene polyterephtalate (Mylar, Terphane) which is transparent to ultrasonic energy vibrational energy. During use a sample solution is entered to the nebulization cell and vibrational energy produced by the transducer is directed by the waveguide structure through the vibrational energy transmitting bath into the nebulization cell where it interacts with the entered sample solution to form sample solution droplets. Said nebulized sample solution droplets are then transported to additional sample preparation stages under the influence of a pressure gradient created by entering a carrier gas flow to the nebulization chamber.

The above summary of relevant references shows that while ultrasonic nebulizer systems provide benefits as compared to other nebulization systems, problems still exist. Problems with operational stability and piezoelectric crystal or equivalent lifetime develop as a result of uneven cooling thereof during use, when bubbles form in a cooling liquid where it meets the piezoelectric crystal or equivalent. In addition, ultrasonic energy produced by a vibrating piezoelectric crystal or equivalent in most ultrasonic nebulizer systems is not well directed for use in nebulizing a sample solution, to a point at which a sample solution is present. Other problems result from injecting a carrier gas meant to carry nebulized sample solution droplets toward a detector in a sample analysis system, at nonoptimum locations and in nonoptimum directions. This leads to formation of turbulance in nebulized sample solution droplet flows and accompanying reagglomeration of nebulized sample solution droplets. This effect is worsened by the presence of relatively small,orifices in the flow paths of nebulized sample solution droplets present in the aerosol chambers of some inventions. Also, the presence of crevasses in the aerosol chamber of some inventions leads to sample carry-over from one analysis procedure to a subsequent analysis procedure. Additional complications result, in some inventions, from the use of pneumatic nebulization means in addition to ultrasonic means, and from the use of system geometry which limits the ultrasonic nebulizer operational frequency to less than megahertz levels.

It should also be understood that sample solution nebulization is typically carried out in an aerosol chamber at a location remote from a sample analysis system, (as described above with respect to ultrasonic nebulizer systems), and nebulized sample droplets must be transported to the location of the sample analysis system by way of a connection means. A common problem which occures during use is that nebulized sample is lost by adherence to the internal walls of the aerosol chamber and connection means between the output of the sample nebulizer system and the input to the sample analysis system. Additionally, the aerosol chamber and connecting means volume must be filled with nebulized sample to cause nebulized sample to eject from said connection means into the remotely located sample analysis system. A relatively larger amount of nebulized sample must then be prepared than would be the case if the sample nebulizer system had no aerosol chamber and was situated in closer proximity to the sample analysis system. System sensitivity is, as a result, adversely affected and tedious, time consuming, system flushing procedures are often required to prevent sample carry-over from one analysis procedure from contaminating subsequent analysis procedure results. It would then, be very beneficial if a sample nebulizer system which did not require an aerosol chamber and which could be positioned closely adjacent to sample analysis systems were available.

Another approach to nebulizing sample utilizes total consumption direct injection micro nebulizing systems such as described in U.S. Pat. No. 4,575,609 to Fassel et al., and by Baldwin and McLafferty, (Org. Mass Spect. 7, 1353, 1973), and by Welderin et al. (Anal. Chem. 63, 219, 1991). A recent Patent to Meyer, U.S. Pat. No. 4,990,740 describes an intraspray torch which serves to overcome some of the problems associated with usage of the Fassel invention. Copending patent applications Ser. No's. 07/813,766 and 07/980,467 of Wiederin, (assigned to CETAC Technologies Inc.), teach improved direct injection micro nebulizers. Direct injection micro nebulizer systems have the important advantage of being able to provide essentially all of the analyte in a sample solution entered thereto, to the detector element in a closely situated sample analysis system. Sample carry-over from one analysis procedure to a subsequent analysis procedure is also minimized by the relatively very small internal volume thereof. Very low flow rate capacity, (e.g. one (1) to one-hundred (100) microliters/min), however, limits the total amount of analyte in a sample solution entered thereto which can reach a detection element in an analysis .system. As a result analysis system sensitivity is not greatly improved by their use. It is noted that sample solution droplet diameters depend on a pressure driven sample solution flow rate.

The Fassel et al. Patent teachings are that the micro nebulizer should be inserted directly into a standard torch of the type used in Inductively Coupled Plasma sample analysis procedures, in which standard torch, during use, a plasma is formed. The micro nebulizer is designed to perform sample solution nebulization directly. That is, the aerosol chamber internal volume and connection means internal volume, between the sample nebulizer system and a remotely located sample analysis system, are eliminated.

The Fassel et al. invention assumes the presence of a first tube, which first tube is essentially the sample injector tube of a inductively coupled plasma standard torch. Briefly, to aid with understanding, said standard torch is comprised of a series of elongated concentric tubes, which concentric tubes are typically, but not necessarily, made of quartz. The centermost tube is typically termed the sample injector tube. It is typically circumscribed by an intermediate tube, which intermediate tube is typically circumscribed by an outer tube. One can visualize the torch system in side elevation, from a position perpendicularly removed therefrom, with the longitudinal dimensions of the various elongated tubes projecting vertically upward from an underlying horizontal surface. Sample particles from a typical sample nebulizing system are typically injected vertically into the sample injector tube of the standard torch from a sample access port at the vertically lower aspect thereof, and caused to flow through said sample injector tube to the upper aspect thereof under the influence of a pressure gradient, whereat they are ejected into the space above said upper aspect of the sample injector tube, which space is typically within the volume circumscribed by the outer tube of the standard torch system, in which space a plasma is typically created during use. As well, typically tangentially injected gas flows are entered into the annular spaces between the outer surface of the sample injector tube and the inner surface of the intermediate tube, and between the outer surface of the intermediate tube and the inner surface of the outer tube. (Note, tangential is to be understood to mean that a gas flow follows a spiral-like upward locus path from its point of entry to the standard torch). The typically tangentially injected gas flows are entered by way of intermediate and outer ports also present in the torch. Said typically tangentially injected gas flows serve to shield the various tubes which they contact from the intense temperatures and heat formed by creation of a plasma in the upper aspects of the torch, and to some extent aid sample flow into the plasma associated area.

The Fassel et al. invention teaches that rather than enter a previously, distally, nebulized sample to the sample access port of a standard torch, a micro nebulizer should be entered into the sample injector tube and positioned so that the upper aspect thereof is at an essentially equal vertical level with the upper aspect of the sample injector tube of the standard torch, into which the micro nebulizer is inserted. Sample solution is then entered into the micro nebulizer via a sample delivery inner tube, directly, without any prior sample nebulization being performed thereon. The Fassel et al. micro nebulizer is designed to cause sample solution entered thereto, to eject from the upper aspect of the micro nebulizer and thereby become nebulized. The upper aspect of the sample delivery inner tube thereof, is positioned at essentially the same vertical level as the upper aspect of the sample injector tube of the standard torch, hence, is located very near the position at which a plasma can be created for use in analysis of the ejected nebulized sample. It will be appreciated that the only nebulizer internal volume which exists is that within the micro nebulizer and the associated connection means thereto from the source of sample solution. Said internal volume is typically on the order of five (5) microliters and is orders of magnitude smaller than the internal volume associated with the sample injector tube of a standard torch and the connecting means thereto from a remotely located conventional sample solution nebulizer system.

To better understand the Fassel et al. micro nebulizer it is necessary to better describe the system thereof. Basically, the Fassel et al. micro nebulizer is comprised of an inner tube and an outer tube, which inner tube is concentrically circumscribed by said outer tube. The two concentric tubes are oriented vertically and placed into the first tube, which first tube can be thought of as the sample injector tube of a standard torch as described above. A sample solution of can be entered into the micro nebulizer at the lower aspect of the inner tube thereof and caused, under the influence of a pressure gradient, (typically 100 to 1000 psi), to flow vertically upward and eject from the upper aspect of the inner tube of the micro nebulizer. Sample solution velocities on the order of one-hundred (100) meters-per-second are common. In addition, a gas flow can be entered into the annular space between the outer surface of the inner tube and the inner surface of the outer tube of the micro nebulizer, which gas flow interacts with the sample solution flow at the point of its ejection from the inner tube of the micro nebulizer, thereby causing said sample solution to be nebulized by essentially pneumatic means. An additional gas flow can be injected into the annular space which results between the outer surface of the outer tube of the micro nebulizer and the inner surface of the sample injector tube of the standard torch into which the Fassel et al. micro nebulizer is inserted. Said additional gas flow can also aid with the sample solution nebulization effect. The nebulized sample solution then immediately injects into the space in the standard torch in which a plasma can be created. The disclosure of the Fassel et al. Patent teaches that a support tube should be epoxied to the outer surface of the outer tube of the micro nebulizer, along some portion thereof which is inside the first tube, (i.e. sample injector tube of the standard torch), during use, apparently to protect the outer and inner tubes thereof against being crushed when inserted into the sample injector tube of the standard torch, and to aid with a firm fit within the sample injector tube of the standard torch into which the micro nebulizer is inserted. The Fassel et al. disclosure teachings also indicate that the outer and inner tubes of the micro nebulizer should be attached to the standard torch by way of a fixed fitting, and that the upper aspect of the inner tube of the micro nebulizer should be positioned vertically at a level below the upper aspect of the sample injector tube of the standard torch. The drawings of Fassel et al. show that the upper aspect of said inner tube of the micro nebulizer is also placed vertically below the upper aspect of the outer tube of the micro nebulizer and that said outer tube of the micro nebulizer and the sample injector tube of the standard torch are tapered inwardly at their upper aspects. In use, it has been found, that the Fassel et al. system as described above, particularly when used with high solids content sample solutions, becomes clogged at the upper aspect thereof. This results in the necessity that the micro nebulizer be cleaned often, which cleaning is difficult to perform and often leads to breakage of the micro nebulizer. It has also been discovered that the upper aspect of the inner tube of the Fassel et al. system is difficult to position inside the outer tube of the Fassel et al. system, and that the Fassel et al. system tends dislodge from the point at which it is secured inside the standard torch sample injector tube at the lower aspect of said sample injector tube, when relatively high pressure gas flow is entered into the annular space between the outer surface of the outer tube of the micro nebulizer and the inner surface of the sample injector tube of the standard torch. It is emphasised that the securing of the micro nebulizer to the inside of the sample injector tube of the standard torch is by way of a fitting, through which fitting is run the outer and inner tubes of the micro nebulizer.

The inventor in the present Application has found that great utility would result from major changes to the Fassel et al. system, which changes would provide means which allow a user thereof to:

1. easily access the inner portion of the upper aspect of the micro nebulizer; and
2. easily insert the inner tube of the micro nebulizer and adjust the vertical location of the upper aspect thereof independent from any interaction with the outer tube thereof.

Other improvements in the Fassel et al. system would result from use of a protective sleeve around at least a portion of the extent of the inner tube thereof, use of hydrofloric acid resistant nonmetalic materials in the construction thereof, and use of a unibody design for the basic portion of the micro nebulizer, which unibody design allows for connections at the lower, middle and upper vertical aspects thereof. The connection at the upper aspect thereof being to allow easy access and cleaning of accumulated sample solids, the connection at the lower aspect thereof being to allow inner tube upper aspect vertical level positioning, and the connection at the middle thereof being to allow attachment to a source of gas to cause a flow thereof into the annular space between the outer surface of the inner tube of the micronebulizer and the inner surface of outer tube thereof, which outer tube thereof would be formed by the unibody design of the micronebulizer. The use of only nonmetalic materials is proposed to prevent untoward interaction with plasma energy which is common when metals are present near a plasma, and the use of hydrofloric resistant materials, (e.g. polyimides), is proposed to allow use of hydrofloric acid as a sample solvent.

Another very recent Patent, No. U.S. Pat. No. 4,990,740 to Meyer, recognizes the benefits and problems associated with the Fassel et al. micronebulizer, and teaches an Intraspray ICP Torch which serves to overcome some of said problems. The Meyer invention, in essence, provides a low operational pressure equivalent to a microneblizer system at the lower aspect thereof, and also provides a series of impactors thereabove in a torch system portion of the invention. The Meyer invention provides greater stability in both construction and in nebulized sample solution flow to an ICP. Said impactors serve to deflect large diameter droplets (e.g. over approximately fifteen (15) microns in diameter), and prevent their ejection from the upper aspect of the invention, and in addition to buffer the ejected flow of nebulized sample solution.

In view of the benefits provided by the Fassel et al. micro nebulizer, and in view of the difficulties associated with use thereof, which difficulties have received recognition from users thereof, there is thus demonstrated a need for an improved direct injection micro nebulizer.

Continuing, as mentioned at the outset, sample preparation for introduction to a detector element in a sample analysis system typically involves not only a sample solution nebulization step, but also sample desolvation and solvent removal steps. Nebulized sample solution droplets are typically desolvated prior to being entered, for instance, to an ICP. If this is not done, plasma instability and spectra emission interference can occur in plasma based analysis systems, and solvent outgassing in MS systems can cause pressures therein to rise to unacceptable levels.

Desolvation of sample solution droplets involves two processes. First, sample solution droplets are heated to vaporize solvent present and provide a mixture of solvent vapor and nebulized sample particles; and second, the solvent vapor is removed. The most common approach to removing solvent is by use of low temperature condenser systems. Briefly, in said low temperature condenser systems the nebulized sample solution droplets are heated to vaporize the solvent present, and then the resulting mixture of solvent vapor and nebulized sample particles is passed through a low temperature solvent removal system condenser. When the solvent present is water very high desolvation efficiency, (e.g. ninty-nine (99%) percent), is typically achieved, when the solvent condensing temperature is set to zero (0) to minus-five (−5) degrees centigrade. However, when organic solvents are present the desolvation efficiency at the indicated temperatures is typically reduced to less than fifty (50%) percent. Use of lower temperatures, (e.g. minus-seventy (−70) degrees centigrade), can improve the solvent removal efficiency, but greater loss of nebulized sample particles by condensing solvent vapor is typically an undesirable accompanying effect. In addition, low temperature desolvation systems typically comprise a relatively large volume condenser. This leads to sample "carry-over" problems from one analysis procedure to a subsequent analysis procedure as it is difficult to fully flush out the relatively large volume between analysis procedures.

A Patent to D'Silva, U.S. Pat. No. 5,033,541 describes a high efficiency double pass tandem cooling aerosol condenser desolvation system which has been successfully used to desolvate ultrasonically nebulized sample droplets. This invention presents a relatively small internal condenser volume, hence minimizes sample carry-over problems, however, while the invention operates at high desolvation efficiencies when water is the solvent involved, it still operates at lower desolvation efficiencies when organic solvents are used. The invention also requires sample passing therethrough to undergo turbulance creating direction reversals, and the use of relatively expensive refrigeration equipments. Turbulance in a nebulized sample flow path can cause reagglomeration of nebulized sample solution droplets and, especially when very low temperatures are present, recapture of nebulized desolvated sample particles present.

A Patent to Skarstrom et al., U.S. Pat. No. 3,735,558 describes a counter-flow hollow tube(s) enclosed filter, mixed fluids key component removal system. Briefly, the invention operates to cause separation of key components from mixed fluids, such as water vapor from air, by entering the mixed fluid at one end of a single, or a series of, hollow tube(s), the walls of which are selectively permeable to the key components of the mixed fluid which are to be removed. A gas is entered to the system at the opposite end of the hollow tube(s), which gas is caused to flow over the outside of the hollow tube(s) in a direction counter to that of the mixed fluids, to provide an external purge of the key components of the mixed fluid which diffuse across the hollow tube(s). Diffusion of key components is driven by pressure and concentration gradients across the hollow tube(s). This approach to removal of diffusing components does not require the presence of low temperature producing refrigeration equipments, and presents a relatively small internal volume.

Two Patents to Vestal, U.S. Pat. Nos. 4,958,529 and 4,883,958 also describe systems which utilize counterflow enclosed filters systems, with the application being to remove solvent vapor from nebulized samples produced by a spraying technique. The Vestal Patents state that the properties of the filter material used are not critical to the operation of the invention, but suggest the use of filter material available under the tradename of ZITEX. Said filter material provides a pore size of from two (2) to five (5) microns with a corresponding porosity of up to sixty (60%) percent. ZITEX is typically available in sheet form and enclosed filters made therefrom are typically constructed from a multiplicity of spacers and two sheets thereof. To provide an enclosed filter which is sufficiently long to provide reliable solvent vapor removal, in a reasonable space, it is typically necessary to arrange the spacers in a pattern which requires many severe sample flow path direction changes. A flow of solvent vapor and nebulized sample particles passing through such a tortuous pathway experiences turbulance. Turbulance causes sample to adhere and accumulate inside the enclosed filter thereby causing sample carry-over problems. The Vestal Patents also describe the heating of the enclosed filter to further assure continuous vaporization of solvent vapor present therein, and the flow of a gas outside the enclosed filter to remove solvent which diffuses through the enclosed filter.

The above presentation shows that the preparation of liquid samples for analysis in gas phase or particle analysis systems typically involves:

1. Nebulizing a sample solution to form sample solution droplets.
2. Desolvating the resulting nebulized sample solution droplets and removal of the solvent.
3. Transporting the sample through the nebulizing system, desolvation and solvent removal systems into a detector of an analysis system.
4. Doing the above with varying degrees of success as regards use with either water or organic solvents, minimizing sample carry-over from one analysis procedure to a subsequent analysis procedure and achieving long term stability of operation.

In view of the above it can be concluded that a sample introduction system which at once: provides high sample solution nebulization efficiency and aerosol conversion rate; produces sample solution droplets with diameters which are determined by an easily controlled independent parameter other than a potentially sample analyte degrading high temperature; is capable, in at least some embodiments, of allowing entry of relatively high sample solution volume flow rate; provides more efficient, (e.g. ninty-nine and nine-tenths (99.9%) percent), desolvation of the produced nebulized sample solution droplets in a manner which is equally successful whether water or organic solvents are present; minimizes sample carry-over by increasing sample transport efficiency therethrough and which optimizes system long term operational stability, would be of great utility. Such a sample introduction system is taught by the present invention.

DISCLOSURE OF THE INVENTION

The need identified in the Background Section of this Disclosure is met by the present invention. The present invention produces nebulized sample solution droplets by use of a high efficiency ultrasonic nebulizer system or by a total consumption direct injection micro nebulizer system, and desolvates the nebulized sample solution droplets produced. Heat is used to vaporize sample solvent in a desolvation system and an enclosed filter solvent removal system system is used to remove vaporized solvent, which enclosed filter solvent removal system is preferably tubular in shape and presents a relatively small internal volume.

Briefly, the ultrasonic nebulizer, (CETAC Technologies Inc. U5000AT (trademark)), of the present invention is comprised of a piezoelectric crystal or equivalent, which is a part of an electric oscillator circuit. The piezoelectric crystal or equivalent is secured in an aerosol chamber encasement in a manner such that no sample retaining crevasses are present. During use the piezoelectric crystal or equivalent is caused to vibrate at, typically but not necessarily, one-and-three-tenths (1.3) Megahertz. A sample solution is caused to impinge upon, or in close proximity to, the vibrating piezoelectric crystal or equivalent and interact with the vibrational energy produced thereby. As a result of said interaction, nebulized sample solution droplets are produced. Recent tests of the high efficiency ultrasonic nebulizer in the present invention system have shown that seventy (70%) percent of said nebulized sample solution droplets formed from a typical sample solution entered thereto have a diameter of thirteen (13) microns or less when the vibrational frequency of the piezoelectric crystal or equivalent is one-and-three-tenths (1.3) Megahertz. At this frequency it is found that a significant increase in uniform production of nebulized sample droplets with small diameters, as compared to droplets produced when lower frequencies are used, is realized. It is noted that in general, as the frequency of vibration of the piezoelectric crystal or equivalent is increased, the smaller will be the theoretical expected average diameter of the nebulized sample solution droplets which are produced. Theoretically, the diameter of droplets formed by ultrasonic nebulization is generally provided by the equation derived by Lang, (see page 78 in "Ultrasound, its Chemical, Physical and Biological Effects, edited by Kenneth S. Suslick, 1988, VCH Publishers):

$$D = 0.34 \times ((8 \times pi \times S)/(FD \times F \times F))^{\frac{1}{3}}$$

where D is diameter, pi is approximated as 3.14, S is surface tension, FD is fluid density and F is frequency of vibration. The droplet formation is considered to result from shocks which originate during cavitation events below the surface of a sample solution, which shocks interact with finite-amplitude capillary surface waves. The present invention thus provides improved sample solution nebulization efficiency over that identified in some of the prior art by identifying a higher ultrasonic nebulizer operating frequency, and making the use thereof practical.

Larger diameter nebulized sample solution droplets produced and present are removed from the system, typically under the influence of gravity, by the way of a drain present in the aerosol chamber in which the piezoelectric crystal or equivalent is present. Remaining relatively small diameter nebulized sample solution droplets are next transported into a desolvation chamber where they are subjected to a heating process at a temperature above that which causes the solvent present to vaporize, thereby producing a mixture of vaporized solvent and nebulized sample particles. Said mixture is next caused to be transported through the previously mentioned enclosed filter, which enclosed filter is of essentially linear geometry, or at worst, of a gradually curving geometry. The sample flow path of the present invention is designed so as not to have any unnecessary constrictions or bends therein. Typically, in the primary embodiment of the present invention, the sample transport alluded to is caused by a pressure gradient induced by entry of a tangentially injected carrier gas into the aerosol chamber near the piezoelectric crystal or equivalent. It is also noted that "tangential" injection is to be understood to mean that the carrier gas follows a spiral-like path locus in the aerosol chamber which is in a direction essentially perpendicular to the surface area of the piezoelectric crystal or equivalent upon which, or in close proximity thereto, a sample solution is caused to be impinged during use. The use of a tangentially directed carrier gas flow reduces sample flow turbulence, hence sample "carryover" and "sample flow" "pulsation" noise producing problems.

The ultrasonic nebulizer of the present invention, as mentioned, provides high efficiency nebulization of sample solutions. The equation of Lang previously presented shows that theoretically a higher frequency of operation is desirable. In view thereof, it should be understood that higher frequencies are not universally used in prior ultrasonic nebulizers because the higher the frequency of operation, the more difficult it is to provide electric power to the piezoelectric crystal or equivalent, and to direct vibrational energy produced thereby to the location of an impinging sample solution. The present invention, as a means to better focusing vibrational energy, provides in the preferred embodiment, a KAPTON (KAPTON is a tradename for a polyimide material) film or equivalent. The KAPTON film or equivalent is positioned behind the piezoelectric crystal or equivalent, with behind taken to mean the side thereof opposite to that upon which a sample solution is impinged during use. Vibrational energy initially directed toward the KAPTON film or equivalent is reflected thereby to a position at which it can be better utilized in the sample nebulization process. The KAPTON film or equivalent serves also as an interface from the piezoelectric crystal or equivalent to a structural heat sink in the aerosol chamber. By providing uniform contact between the piezoelectric crystal or equivalent and the heat sink, efficient and uniform heat removal from the piezoelectric crystal or equivalent is achieved during use. In conjunction with the use of air cooling, this leads to more stable ultrasonic nebulizer performance and longer piezoelectric crystal or equivalent lifetime. The KAPTON film or equivalent also is compressible. By interfacing the piezoelectric crystal or equivalent to the structural heat sink by way of a KAPTON film or equivalent (or multiple layers thereof), the piezoelectric crystal or equivalent is "cushioned" as it vibrates. That is, it does not undergo repeated direct contact with the relatively rigid structural heat sink. This leads to further increases in the piezoelectric crystal or equivalent lifetime, said lifetime being on the order of years rather than weeks, as is the case for piezoelectric crystals or equivalents in some earlier ultrasonic nebulizer systems. The present invention, in the preferred embodiment thereof, also provides a glass insulator on the front of the piezoelectric crystal or equivalent to protect it against corrosion etc. by components present in samples impinged thereon.

Continuing, the total consumption Direct Injection Micro Nebulizer System of the present invention, (CETAC Technologies Inc. MICRONEB-2000 (trademark)), comprises a system which can be inserted into the space within a sample injector tube of a standard torch, as described with respect to the Fassel et al. invention in the Background Section of this Disclosure, or into specially designed torches which, for instance, have no sample injector tube present, to form direct injection micro nebulizer based sample introduction and analysis systems. The present invention accepts a sample solution which has not been subject to prior nebulization and typically injects it into a closely situated plasma in a sample analysis system, performing required sample solution nebulization directly, again much as taught in the Fassel et al. Patent. The present invention, however, provides utility not taught in Fassel et al. and can be used in sample analysis systems other than those utilizing torches and plasmas, including those which include sample desolvation and solvent removal systesm as it does not require the presence of an ICP torch sample injector tube as part of its construction.

The present invention is, in its preferred embodiment, comprised of a system of a primary body element, a top element, a double nut element system, or functionally equivalent sample delivery tube system adjustment means, and a sample delivery tube which is typically encompassed within a separate or integral protective sleeve over at least a portion of its length, to form the sample delivery tube system.

The primary body element of the present invention is preferably, but not necessarily, of unibody construction and is generally elongated in shape with a distinct longitudinal dimension, and with a centrally located longitudinally oriented hole extending therethrough. At the upper aspect of the primary body element, as it is viewed in side elevation from a position perpendicularly removed therefrom, with the longitudinal dimension thereof projecting vertically upward, perpendicular to an underlying horizontal surface, is located a first connection means, which first connection means typically comprise female screws threads. (Note that the direct injection micro nebulizer need not be oreinted as just described to facilitate discussion, during use). A top element, which has a centrally located longitudinally oriented hole therethrough and which has connection means which are complimentary to said first connection means at the upper aspect of the primary body element, is also typically present and removably attached to the primary body element by way of said connection means. The top element can be of an elongated design which provides means for positioning the upper aspect of the top element near a plasma in an inductively coupled plasma torch, while maintaining an attached primary body element of the direct micro injection nebulizer system at some distance therefrom. The top element can also have a saphire or functionally equivalent, ultraviolet transparent, non-heat conducting, high strength, tight tolerance inner diameter top element tip component present at its upper aspect. In addition, a circumscribing tube can be present which forms an annular space around the top element, through which annular space a gas of a desired temerature can be caused to flow, via a modified top element port, during use. The purposes of the top element tip component and the circumscribing tube include allowing effecting better transport of sample through the total consumption direct injection micro nebulizer during use, hence, reducing sample deposition and accumulation, (i.e. clogging etc.), problems. At the lower aspect of the primary body element there is present a second connection means, again comprising, typically, female screw threads. A double nut element system, or functionally equivalent sample delivery tube system adjustment means, which has a centrally located longitudinally oriented hole therethrough and which has connection means thereon, which connection means are complimentary to the second connection means at the lower aspect of the primary body element, is also present and removably attached to the primary body element by way of said second connection means. In one embodiment of the present invention a chromatography column can be attached to the sample delivery tube system, typically at the lower aspect of the sample delivery tube system adjustment means, to allow temporal preseparation of sample components in a multi-analyte component sample solution prior to entry thereof into the direct injection nebulizer system. (Note, a chromatography column causes various analyte components in a sample solution to move therethrough, as the containing sample solution is passed therethrough, at varying rates based upon, for instance, varying affinities for the various components by the materials present in the chromatography column.) In another embodiment of the present invention the sample delivery tube system adjustment means is fixed and adjusted only at manufacture or during iniatial user utilization. Also present on said primary body element is a third connection means which provides access to the centrally located longitudinally oriented hole which projects through the primary body element.

The sample delivery tube of the present invention is typically but not necessarily, over at least the portion of its length extending from the lower aspect of the sample delivery tube system adjustment means, encompassed within a separate or integral protective sleeve, and the combination sample delivery tube and optional protective sleeve, (or in some cases only the sample delivery tube per se), forming a sample delivery tube system, is threaded into the centrally located longitudinally oriented hole through the double nut element system, or functionally equivalent sample delivery tube system adjustment means. The sample delivery tube per se, (i.e. the sample delivery tube system without a protective sleeve), is then, typically, threaded through the centrally located longitudinally oriented hole through the primary body element, then into and out of the centrally located longitudinally oriented hole through the top element, when said top element is present. The top element, when present, is then removably attached to the primary body element by way of the connection means thereon which are complimentary to the first connection means present at the upper aspect of the primary body element. It should be noted that inserting the sample delivery tube into the centrally located longitudinally oriented hole which extends through the top element prior to removably attaching it to the upper aspect of the primary body element at the first connection means thereon facilitates the direct injection micro nebulizer system construction process. At the lower aspect of the direct injection micro nebulizer system the sample delivery tube system is removably attached to the primary body element, via the upper oriented nut of the double nut element system, or functionally equivalent sample delivery tube system adjustment means, by way of the second connection means present at the lower aspect of the primary body element. The lower nut of the double nut element system firmly grips the sample delivery tube system, and removably attaches to the upper nut of the double nut element, or functionally equivalent sample delivery tube system adjustment means, system by way of connection means thereon. It should be understood that the vertical level of the upper aspect of the sample delivery tube can then be easily adjusted by a user of the present invention by manual or automated manipulation of the upper nut of the double nut element system, or functionally equivalent sample delivery tube system adjustment means which has not been fixed in position, where it removably attaches to second connection means at the lower aspect of the primary body element of the direct injection micro nebulizer system taught herein.

During use with a standard torch and plasma sample analysis system, the present invention, as described above, is inserted into and secured within, the space within the sample injector tube of a standard torch, or within the intermediate tube of a specially designed torch which has no sample injector tube present for instance, such that the upper aspect of the sample delivery tube is positioned, typically, just below the position therein at which a plasma can be created for use in the analysis of samples. The vertical level of the upper aspect of the sample delivery tube can be precisely adjusted by manipulation of the double nut element system, or sample delivery tube system adjustment means functional equivalent, as alluded to above. A sample solution is entered into the sample delivery tube, at the end thereof opposed to that present at the upper aspect of the present invention. Said sample solution is forced to move through the sample delivery tube and eject from the upper aspect thereof. Said flow is typically effected by a pressure gradient, but can also be effected by application of an electrical gradient. In addition, a gas flow is caused to be entered to the third connection means on the primary body element. Said gas flow, under the influence of a pressure gradient, transverses the length of the primary body element in the annular space between the outer surface of the sample delivery tube and the inner surface of the centrally located longitudinally oriented hole through primary body element. At the upper aspect of the primary body element, or the upper aspect of the top element if present, said gas flow is ejected from from the annular space between the outer surface of the sample delivery tube and the inner surface of the centrally located longitudinally oriented hole through the top element. The ejected sample solution interacts with said ejected gas flow to effectively nebulize the sample solution into sample solution droplets. In addition, an auxiliary sample gas flow can be entered into the annular space between the outer surface of the primary body element of the present invention, and the inner surface of the sample injector tube of the standard torch, if present, by way of an access port in the standard torch. Specially designed top elements can include a circumscribing tube and modified top element port to allow a similar effect in torches which have no sample injector tube present. Said gas flow, again typically under the influence of a pressure gradient, will eject from the annular space into which it is entered, and interact with the simultaneously ejected sample solution, and optionally, a gas flow as described above which is entered to the third connection means of the primary body element. The overall effect being to provide finely nebulized sample solution droplets, and cause same to be vertically swept into the region of the standard, or specially designed, torch in which a plasma can be created. If a specially designed torch which has no sample injector tube present is used, the additional gas flow just described, will of course, not be possible but can be approximated if the modified top element alluded to above is present. This arrangement is better described in the Detailed Description Section herein.

The present invention additionally, in the preferred embodiment thereof, is fabricated from hydrofloric acid resistant nonmetallic materials, and the primary body element is firmly but removably secured within the sample injector tube of the standard, or intermediate tube of a specially designed, torch with which it is used, by means of one or more "O" rings which circumscribe the primary body element. As well, an essentially tubular shaped, strength providing, top element tip component which provides a tight tolerance inner diameter, is transparent to microwave radiation, not susceptible to heating and which is resistant to sample deposition and accumulation during use, can be present at the upper aspect of a top element. A typical top element tip component will be constructed from saphire tubing or functional equivalent.

It will be appreciated that the present invention allows a user thereof to easily access the inner space at the upper aspect of the primary body element when the top element is removed. This feature allows easy cleaning of any solid sample build up at said location which might clog the invention. In addition, threading the sample delivery tube into the centrally located longitudinally oriented hole through the top element, when it is present, can be easily performed when the top element is removed from the first connection means at the upper aspect of the primary body element. Also, as alluded to above, the vertical level of the upper aspect of the sample delivery tube can be easily and precisely adjusted by manipulation of the upper nut element of the double nut system, or by manipulation of a sample delivery tube system adjustment means which is not fixed in position, at its attachment to the second connection means on said primary body element. In some embodiments, however, the sample delivery tube adjustment means is adjusted only during manufacture or during initial user utilization. That is, a sample delivery tube can be permanently fixed in place by a plug-like, (which can be a fused double-nut system), element which is firmly secured at the lower aspect of the primary body element, which plug-like element firmely grips the sample delivery tube and fixes it in relationship to the primary body element.

While the use of a standard or specially designed torch, such as typically used in Inductively Couples Plasma analysis of samples was used as an example in the above, it is to be understood that the present invention could also be used to introduce sample into, for instance, a mass spectrometer sample analysis system, perhaps by way of a desolvation and/or solvent removal systems. In such a system momentum separators, skimmers, enclosed filters, roughing pumps and ion focusing lenses etc. might be present. That is to say the present invention can be used with sample analysis systems which require sample nebulization, other than sample analysis systems which utilize standard or specially designed ICP torches and plasmas.

Continuing, as alluded to above, the present invention uses an enclosed filter solvent removal system, and the properties of the enclosed filter material composition have been found to be of importance to the operation thereof. The enclosed filter is made from a material which allows the solvent vapor to diffuse therethrough, but which retains the nebulized sample particles therein. In the preferred embodiment of the present invention the material is GORE-TEX, (GORE-TEX is a tradename), micro porous PTFE tubing, manufacturer part No. X12323, No. X12499 or No. X12500. Said GORE-TEX microporous PTFE tubing has inner diameters of approximately four (4), two (2) and one (1) millimeters respectively. Said GORE-TEX microporous tubing filter material is preferred as it simultaneously provides high porosity (e.g. seventy (70%) percent) and small pore size, (e.g. one (1) to two (2) microns). The higher the porosity of a material, the easier it is for solvent vapor to diffuse therethrough, and the smaller the pore size of a material, the smaller the nebulized sample particles can be and still be retained within an enclosed filter made thereof as they are transported therethrough. It is difficult to obtain both high porosity and small pore size in a filter material, but said combination has been achieved in the GORE-TEX product and use of same allows shorter length enclosed filters to be used which provide excellent solvent vapor removal characteristics. It should be apparent that a shorter enclosed filter length provides a smaller enclosed volume inside said enclosed filter, and that translates into a reduced chance for nebulized sample particles to adhere to and accumulate within same during use at reasonable sample flow rates therethrough. The present invention operates quite well when the enclosed filter length is forty (40) centimeters or less in length. Said enclosed filter length is five (5) or more fold shorter than enclosed filters providing equivalent desolvation capability which are made from other materials, (e.g. filter material available under the tradename of ZITEX for instance). Continuing, the solvent vapor which diffuses across the enclosed filter is flushed out of the system, typically by a flow of gas outside the enclosed filter, while the nebulized sample particles are transported into a sample analysis system, typically under the influence of the pressure gradient which is created by entering of the tangentially injected carrier gas to aerosol chamber of the system near the ultrasonic nebulizer piezoelectric crystal or equivalent, as mentioned above. Note, however, that it is within the scope of a modified embodiment of the present invention to remove solvent vapor which diffuses through the enclosed filter by use of a low temperature condenser through which the enclosed filter extends rather than by way of a flow of gas outside the enclosed filter. If this is done the enclosed filter is maintained at a temperature above that of the solvent involved to prevent solvent condensation and sample analyte deposition and accumulation inside the enclosed filter. The low temperature condenser is, however, maintained below the condensation point of the solvent present. Also, if this is done the pressure gradient which drives the nebulized sample particles transport will typically be created by use of vacuum pumps which reduce pressure at the outlet, sample analysis end of the enclosed filter, and the tangentially injected carrier gas flow mentioned above will not be present.

Continuing, when a solvent removal gas flow outside the enclosed filter is used to remove diffused solvent vapor the flow rate thereof is typically set to approximately one (1) liter per minute when the carrier gas flow is set to approximately one-half (0.5) liters per minute and when the sample solution flow into the ultrasonic nebulizer is approximately one (1) mililiter per minute. With said parameters the solvent vapor partial pressure difference across the enclosed filter membrane is kept to an optimum level by quickly removing solvent vapor which diffuses across the enclosed filter membrane. In addition, it must be understood that it is important to keep the enclosed filter temperature above the boiling point of the solvent involved to prevent condensation of solvent vapor therein. When water is used as a solvent the temperature is kept at one-hundred-and-twenty (120) degrees Centigrade or above.

It is also mentioned that use of solvents with boiling points well below the temperature at which a sample of interest evaporates serves to optimize operation of the present invention, and that the present invention is equally effective in desolvating water or organically solvated samples.

The present invention will be better understood by reference to the Detailed Description Section of this Disclosure and the accompanying drawings.

SUMMARY OF THE INVENTION

The capability of gas phase and particle sample analysis systems such as those which use Inductively Coupled Plasmas (ICP's) and Mass Spectrometers (MS) for example, to analyze samples entered thereto is well known. Typically, a sample solution is entered to a sample analysis system by way of sample nebulizing, desolvating and solvent removal systems. The use of pneumatic and mechanical means to nebulize sample solutions and the use of low temperature condensers to remove solvent from resulting nebulized sample solution droplets, which have been heated to vaporize the solvent present, are generally taught. Such desolvating and solvent removal systems, however, are generally not as efficient when an organic solvent is present, as compared to when water is the solvent.

Also taught in various references is the use of ultrasonic nebulizers to nebulize samples. Ultrasonic nebulizers generally comprise a piezoelectric crystal or equivalent which is caused to vibrate. A sample solution is caused to impinge thereon, or in close proximity thereto, inside an aerosol chamber and interaction between the vibrational energy produced by the vibrating piezoelectric crystal or equivalent and the impinging sample solution causes the later to be nebulized into nebulized sample solution droplets. Some ultrasonic nebulizers taught in the prior art, however, typically operate at relatively low frequencies, (e.g. in the kilohertz range), and provide less than optimum sample solution nebulization. Recent tests of the present invention ultrasonic nebulizer system, (CETAC Technologies U5000AT (trademark)), however, have shown that seventy (70%) percent of the sample solution droplets formed thereby have a diameter of thirteen (13) microns or less when the operational frequency is set to one-and-three-tenths (1.3) megahertz.

The high efficiency ultrasonic nebulization system of the present invention includes, in the preferred embodiment, a KAPTON, (KAPTON is a tradename for a polyimide material), film or equivalent, between the piezoelectric crystal or equivalent and a structural heat sink in an aerosol chamber which houses the piezoelectric crystal or equivalent. The Kapton film or equivalent serves to reflect vibrational energy, not initially so directed, to a location at which it can be better utilized in nebulizing impinging sample solution. The KAPTON film or equivalent also serves as a uniform contact interface between the piezoelectric crystal or equivalent and the structural. Said KAPTON film or equivalent interface provides uniform heat removal from the piezoelectric crystal during use, and serves as a compressible material to buffer contact between the piezoelectric crystal or equivalent and the relatively rigid structural heat sink. The presence of the KAPTON film or equivalent serves to increase the operational efficiency of the present invention and lifetime of the piezoelectric crystal or equivalent. The present invention also uses air cooling by way of the structural heat sink.

Sample nebulizers, ultrasonic nebulizers included, typically nebulize a sample solution in an aerosol chamber at a location distally situated from a sample analysis system, such as an inductively coupled plasma or mass spectrometer sample analysis system. As a result the nebulized sample must be transported to the sample analysis system through a relatively large internal volume connection means. The aerosol chamber and connection means internal volume is the source of numerous problems. For instance, its presence dictates that a relatively large amount of nebulized sample solution be available to fill same. The sensitivity of the overall sample analysis system is thus reduced. Additionally, said internal volume must often times be flushed out after an analysis procedure to prevent contamination of results obtained in subsequent analysis procedures.

In view of the above identified problems inventors have developed and Patented a Micro Nebulizer for Direct Injection of Samples to a sample analysis system. See U.S. Pat. No. 4,575,609 to Fassel et al. Said Micro Nebulizer is, during use, placed, and performs nebulization, very near associated sample analysis equipment, which in the case of the Fassel et al. invention involves placement in the sample injector tube of an inductively coupled plasma sample analysis system standard torch. The internal volume of the micro nebulizer is, as a result, kept very small, typically on the order of five (5) microliters. The overall effect is that the sensitivity of an overall system using the Fassel et al. micro nebulizer is increased and the "carry-over" of sample from one sample analysis procedure to a subsequent sample analysis procedure is easier to prevent because there is less internal volume to flush out between analysis procedures.

Users of the Fassel et al. micro nebulizer have found, however, that certain design features thereof make it inconvenient to use. For instance it is difficult to clean the device without completely breaking it down, and it is difficult to adjust the upper aspect of the inner tube, which inner tube carries a sample solution flow, with respect to the upper aspect of the outer tube thereof. It is noted that the annular space between the outer surface of the inner tube and the inner surface of the outer tube provides a pathway through which a gas flow is maintained during use of the micro nebulizer. Said gas flow interacts with the sample solution flow at the location at which both flows simultaneously eject from the upper aspect of the micro nebulizer to cause the sample solution to be nebulized into sample solution droplets. The two flows alluded to, it will be appreciated, must eject at proper orientations with respect to one another or proper sample solution nebulization is not achieved. The utility of an ability to easily manually or automatically adjust the vertical location of the upper aspect of the inner tube with respect to that of the outer tube should then be appreciated. It has also been found that the inner tube of the Fassel et al. invention can be easily crushed, for example when the invention is being cleaned. A separate or integral protective sleeve which covers at least a portion thereof would therefore provide utility. Additionally, it is taught herein that the major element of the direct injection micro nebulizer system should preferably be of one piece unibody construction, should contain no metallic parts and be of a material which is resistant to degradation by hydrofloric acid. Essentially unibody design would allow use of the system with other than ICP torches for instance and the use of nonmetallic parts avoids the occurance of untoward effects when the invention is placed near an inductively coupled plasma. Use of hydroflouric acid resistant material is preferred as samples to be nebulized at times are solvated by a solvent containing hydrofloric acid or the fact that hydrofloric acid is sometimes used as a cleaning agent in analysis systems.

For emphasis, it is again stated that the present invention provides that the direct injection nebulizer system should be designed to allow use with not only standard ICP torch sample analysis systems, but also with ICP torches which have no sample injector tube present or with other sample analysis systems such as mass spectrometer sample analysis systems. That is, the direct injection micro nebulizer system should not require attachment to the sample injector tube of a standard ICP torch to be utilized. In particular, the present direct injection nebulizer can be combined with an enclosed filter solvent removal system to effectively substitute for the ultrasonic nebulizer system discussed above.

An improved micro nebulizer system, termed a Direct Injection Micro Nebulizer System, is thus taught herein, which serves to overcome the problems inherent in the use of the Fassel et al. invention and which expands the potential uses thereof.

Various References also teach the use of relatively small volume enclosed filters which allow solvent vapor to diffuse therethrough, but which retain nebulized sample particles which result from the desolvation of nebulized sample solution droplets, therein. Said references do not, however, emphasise that the properties of the material from which an enclosed filter is fabricated, or enclosed filter geometry are critical to system performance. In addition, no known reference teaches that high efficiency ultrasonic nebulizer systems can, or should, be used in conjunction with relatively small volume high efficiency enclosed filter solvent removal systems.

The present invention provides a sample introduction system which combines a highly efficient ultrasonic or direct injection micro nebulizer sample nebulization system with a highly efficient, typically but not necessarily, geometrically linear, relatively small internal volume, enclosed filter solvent removal system. In use nebulized sample droplets formed by the ultrasonic or direct injection micro nebulizer are desolvated by being subjected to heat in a desolvation system and are then caused to be transported through the enclosed filter and then into a sample analysis system. Solvent vapor diffuses through the enclosed filter and is removed, typically, by a flow of gas outside said high efficiency enclosed filter. In some applications a low temperature condenser, (rather than a solvent removal gas flow outside the enclosed filter), through which the enclosed filter passes might be used to condense and remove said diffused solvent vapor, while the enclosed filter temperature is maintained above the boiling point of the solvent involved. This might be done, for instance, when a mass spectrometer analysis system is used with the present invention.

The relatively small volume enclosed filter desolvation system is, in the preferred embodiment, comprised of small diameter tubing (e.g. one (1) to four (4) millmeters), fabricated from high porosity, small pore size material, typically GORE-TEX, (GORE-TEX is a tradename), Micro porous PTFE tubing. As a result the present invention provides an efficient sample nebulization system in conjunction with a solvent removal system which minimizes sample carry-over from one analysis procedure to subsequent analysis procedures, said carry-over being associated with relatively large desolvation condenser volumes, and even relatively small volume enclosed filter solvent removal systems which make use of inferior filter materials and/or relatively tortuous sample flow path enclosed filter geometries. The present invention also provides a system which does not cause nebulized sample particle recapture during desolvation and solvent removal. This is the result of maintaining the enclosed filter temperature above the boiling point of the solvent involved. It is also emphasized that the desolvation system of the present invention works equally well with water or organic based solvents.

It is therefore a purpose of the present invention to provide a system for introducing samples to sample analysis systems which utilizes efficient sample nebulization means.

It is another purpose of the present invention to provide a system for introducing samples to sample analysis systems which utilizes efficient nebulized sample solution droplet desolvation and solvent removal means, It is yet another purpose of the present invention to provide a system for introducing samples to sample analysis systems which minimizes sample carry-over from one sample analysis procedure to a subsequent analysis procedure, It is still yet another purpose of the present invention to provide a system for introducing samples for entry to sample analysis systems which efficiently transports sample therethrough, It is another purpose of the present invention to provide a system for introducing samples to sample analysis systems which is equally efficient in desolvating nebulized sample solution droplets whether water or organic solvents are present, It is yet another purpose of the present invention to provide an ultrasonic nebulization system in which the piezoelectric crystal or equivalent is interfaced to an air cooled structural heat sink by a KAPTON or equivalent film, It is still yet another purpose of the present invention to provide a system for introducing samples to sample analysis systems which demonstrates stable operation and long component lifetimes, It is another purpose of the present invention to provide a system for introducing samples to sample analysis systems which causes sample transport therethrough by entry of a carrier gas flow and/or by application of a low pressure at the sample analysis system extent of said system, It is yet another purpose of the present invention to provide a direct injection micro nebulizer system which is easy to clean.

It is yet still another purpose of the present invention to provide a direct injection micro nebulizer system in which adjustment of the vertical location of the upper aspect of the inner, sample delivery, tube with respect to the outer tube, (termed a primary body element in the present invention), is, in the preferred embodiment, easy to carry out.

It is yet another purpose of the present invention to teach a direct injection micro nebulizer system which is constructed from nonmetalic and/or hydrofloric acid resistant materials.

It is still yet another purpose of the present invention to teach a direct injection micro nebulizer system which provides one piece or unibody construction of the major element, the primary body element, of the invention.

Still yet another purpose of the present invention is to teach the optional use of a separate or integral protective sleeve on the sample delivery, (i.e. inner tube of Fassel et al. invention), tube to form a crush resistant sample delivery tube system.

Yet still another purpose of the present invention is to teach a direct injection micro nebulizer system which can be used in sample analysis systems which do not provide a sample injector tube of a standard ICP torch as an element thereof.

BRIEF DESCRIPTION OF THE DRAWINGS

FIG. 1 shows the entire system of the primary embodiment of the present invention utilizing an ultrasonic nebulizer system, in diagramatic form.

FIG. 2a shows a preferred embodiment of a solvent removal system of the present invention, in diagramatic form.

FIG. 2b shows an expanded scale cross sectional view taken at a—a in FIG. 2a.

FIG. 3 shows an expanded view of the preferred arrangement of vibrational energy producing associated elements in the ultrasonic nebulizer of the present invention. A KAPTON film or equivalent, piezoelectric crystal or equivalent, insulator and "O" ring are shown in exploded form for easier observation.

FIG. 12a shows an alternate embodiment of a top element of the modified embodiment of the direct injection micro nebulizer of FIG. 9, in which a circumscribing tube provides an annular space through which a gas can be caused to flow during use to aid sample flow through the direct injection micronebulizer.

FIG. 12b shows a partial view of the top element of FIG. 12a placed into a torch with a port present thereon which allows entering a gas flow into the annular space of FIG. 12a.

DETAILED DESCRIPTION

Figure 4:
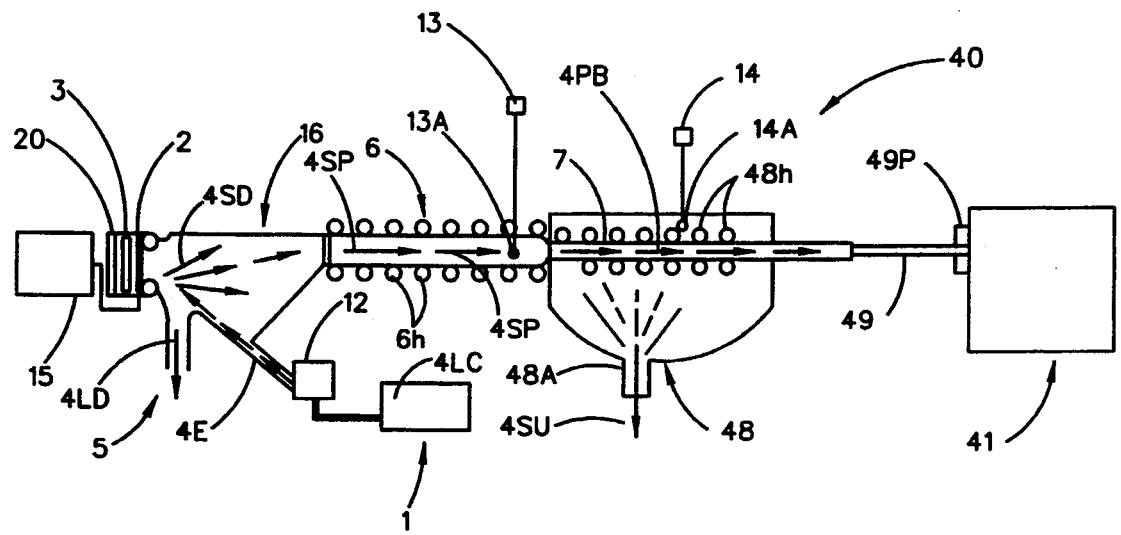
FIG. 4 shows the entire system of a modified embodiment of the present invention utilizing an ultrasonic nebulizer, in diagramatic form.
Figure 5:
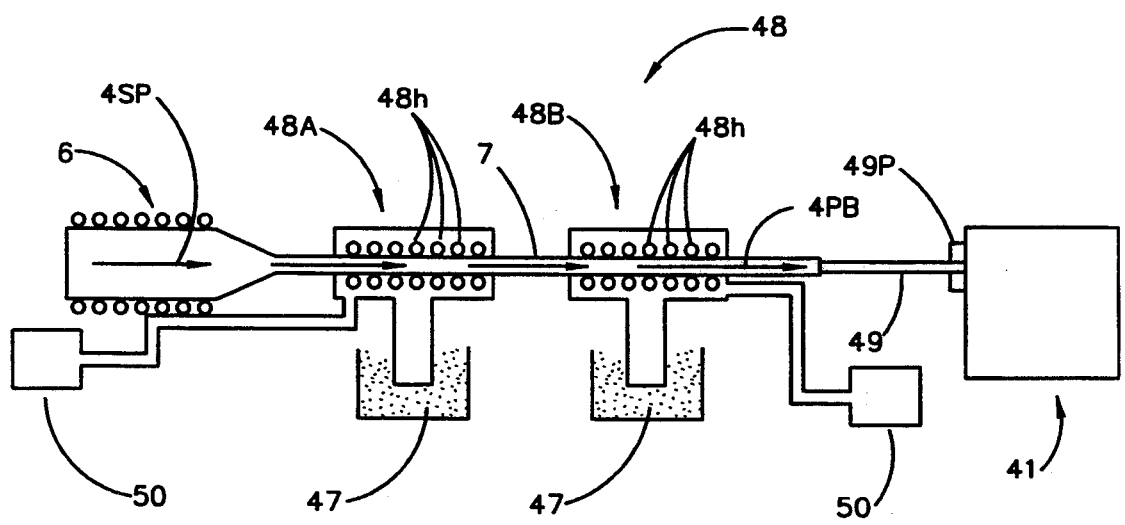
FIG. 5 shows a second embodiment of a solvent removal system of the present invention, in diagramatic form.

Turning now to the Drawings, there is shown in FIG. 1 a diagramatic view of one embodiment of the overall system of the present ultrasonic nebulizer and enclosed filter solvent removal sample introduction invention (10). A source (1) of sample solution (4LC) is shown attached to means (12) for causing said sample solution (4LC) to impinge upon piezoelectric crystal or equivalent (2) in aerosol chamber system (16). (The sample solution (4LC) can originate from any source of liquid sample). The aerosol chamber (16) provides essentially tubular means for entering a sample solution flow thereto and an impinging sample solution flow is identified by numeral (4E), the flow rate of which is typically, but not necessarily one (1) mililiter per minute. Piezoelectric crystal or equivalent (2) is caused to vibrate, typically but not necessarily at one-and-three-tenths (1.3) Megahertz, by inclusion in an electric power source and oscillator circuit (15). Also shown is a KAPTON film or equivalent (KAPTON is a tradename for a polyimide material) (3) which serves to reflect and help focus vibrational energy developed by piezoelectric crystal or equivalent (2) to the location thereon, or in close proximity thereto at which the sample solution (4E) impinges, in front of said piezoelectric crystal or equivalent (2). Said KAPTON film or equivalent (3), also serves as a compressible buffer means by which the piezoelectric crystal or equivalent (2) is attached to the aerosol chamber system (16) structural heat sink (20). The aerosol chamber provides an essentially tubular structural heat sink connection means, (including other than circular cross section geometry), with a constriction, (understood to include functional equivalents), present therein. FIG. 3 shows an expanded view of the structural heat sink (20) at its point of connection to the aerosol chamber (16). FIG. 3 also shows in exploded fashion the KAPTON film or equivalent (3), the piezoelectric crystal or equivalent (2) and an insulator (2S) which is typically, but not necessarily, made of a glass material, present on the front surface of the piezoelectric crystal or equivalent (2). The purpose of the insulator (2S) is to protect the piezoelectric crystal or equivalent against corrosion etc. due to components in sample solutions impinged thereon. Also note by reference to FIG. 3 that when the structural heat sink (20) is slid fully into the aerosol chamber (16), the KAPTON film or equivalent (3), piezoelectric crystal or equivalent (2) and insulator (2S) will be sandwiched together between the structural heat sink and the constriction in the structural heat sink connection means in the aerosol chamber. Also note that "O" ring (2R) will then serve to prevent crevasses from existing at the point of connection between the aerosol chamber (16) and the vibrational energy producing elements of the invention. Crevasses, as mentioned in the Background Section of this Disclosure, in other ultrasonic nebulizing systems have led to sample carry-over problems. It is mentioned that electrical contact to the piezoelectric crystal or equivalent (2) from the electric oscillator circuitry (15) can be by any convenient connector pathway, and is typically by way of an opening in the structural heat sink (20). Also note in FIG. 3 the indication of cool air flow (20A) over fins in the structural heat sink (20). Said fins are located distally to the point of the structural heat sink which contacts the KAPTON film or equivalent. The present invention uses air cooling and thereby avoids the complications associated with liquid cooling systems discussed in the Background Section of this Disclosure. Continuing, the compressible nature of the KAPTON film or equivalent (3) material prevents the piezoelectric crystal or equivalent (2) from repeatedly vibrating against the rigid aerosol chamber system (16) or structural heat sink (20) to which it is interfaced during operation. Said buffering prevents damage to the piezoelectric crystal or equivalent (2). Also, when the KAPTON film or equivalent (3) is in place it acts as a uniform contacting heat conducting interface between the vibrating piezoelectric crystal or equivalent (2) and the aerosol chamber system (16) or structural heat sink (20). Uniform heat removal, and piezoelectric crystal or equivalent (2) to aerosol chamber (16) and structural heat sink (20) vibrational contact buffering during use, serve to stabilize the operation of and prolong the lifetime of the piezoelectric crystal or equivalent (2) of the present invention. Typically a lifetime of years, rather than weeks (as is typically the case with piezoelectric crystals or equivalent in other ultrasonic nebulizer systems), is achieved. As mentioned above that the piezoelectric crystal or equivalent (2) of the present invention is, in the preferred embodiment, cooled by flowing air past structural heat sink (20). That is, no liquid coolant is required. As a result, corrosion problems associated with liquid cooled ultrasonic nebulizers as disclosed in the Background Section of this Disclosure are eliminated.

Continuing, interaction between vibrational energy produced by said piezoelectric crystal or equivalent (2) and impinging sample solution (4E) causes production of nebulized sample solution droplets (4SD). Seventy (70%) percent of said nebulized sample solution droplets are typically of a diameter of less than thirteen (13) microns when the frequency of vibration of the piezoelectric crystal or equivalent in the present invention is one-and-three-tenths (1.3) Megahertz. Larger diameter droplets (4LD) typically fall under the influence of gravity, and are removed from the system (10) at drain (5) of aerosol chamber system (16). The remaining smaller diameter nebulized sample solution droplets (4SD) are caused to flow, typically under the influence of a pressure gradient created by entering a typically tangentially directed carrier gas flow "CG" at essentially tubular carrier gas inlet port (9), into desolvation chamber (6) in which the temperature is caused to exceed the boiling point of the solvent which is present, by heater means (**6*h*). The carrier gas "CG" flow rate is typically one-half (0.5) liters per minute. In said desolvation chamber (6) the nebulized sample solution droplets are desolvated to form a mixture of solvent vapor and nebulized sample particles (4SP). It is mentioned that a tangentially oriented carrier gas flow which follows a spiral-like path locus which is essentially perpendicular to the surface of the piezoelectric crystal or equivalent (2) and toward desolvation chamber (6), helps to prevent sample "carry-over" and "pulsation" problems, as discussed in prior sections of this Disclosure. It is again mentioned that no crevasses are present in the aerosol chamber which can retain sample. Continuing, the mixture of solvent vapor and nebulized sample particles (4SP) is caused to flow, typically under the influence of the pressure gradient created by entering carrier gas flow "CG", into an enclosed filter (7) of solvent removal system (8). Heater means (8*h*) serve to keep the temperature in the solvent removal system (8**) above the boiling point of the solvent present. Typical temperatures maintained within the solvent removal means are in the range of fourty (40) and one-hundred-and-fifty (150) degrees centigrade, depending on the solvent being used.

Enclosed filter (7) is made of a material which allows solvent vapor to diffuse therethrough, but which retains the nebulized sample particles therein. A solvent vapor removing gas flow "A" is caused to enter solvent removal system (8) at inlet port (**8*a*), flow around the outside of enclosed filter (7), and exit at outlet port (8*b*). Said solvent vapor removing gas flow is indicated as "A" at the inlet port (8*a*) and as "A'" at the outlet port (8*b*). Said solvent vapor removal gas flow serves to remove solvent vapor which diffuses through said enclosed filter (7). The nebulized sample particles (4SP) which remain inside of enclosed filter (7) are then caused to flow, typically under the influence of the above identified pressure gradient, into an Inductively Coupled Plasma analysis system, or other analysis system (11) by way of connection means (11C). Said flow is identified by the numeral (4PB**).

It is mentioned that enclosed filter (7) is typically made of PTFE material and is available under the tradename of GORE-TEX. Said material has a pore size of one (1) to two (2) microns and a porosity of seventy (70%) percent. Tubular forms of the filter are available with one (1), two (2) and four (4) milimeter inner diameters and are identified as GORE-TEX micro porous tubings. Said microporous tubular filters are especially suitable for use in the present invention. The GORE-TEX PTFE material has been found to provide the present invention with improved operating characteristics by allowing a relatively short length, (e.g. less than fourty (40) centimeters), of enclosed filter to be used, while still allowing efficient removal of solvent vapor. Enclosed filters made of other commercially available materials must typically be five (5) or more fold longer to provide equivalent solvent removal capability. A shorter length of enclosed filter means that the enclosed filter contains a smaller volume and, hence, that sample "carry-over" from one analysis procedure to a subsequent analysis procedure is greatly reduced. In addition, said enclosed filter, being of essentially linear geometry or at worst requiring only gradual curves, (eq. a coiled configuration), therein to fit into reasonably sized system containments, does not present a sample transported therethrough with turbulance creating severe direction reversals. Longer enclosed filters made from inferior pore size and porosity parameter filter materials typically do include such turbulence creating sample flow path direction reversals. The result is increased sample "carry-over" based problems during use.

Also shown in FIG. 1 are desolvation chamber and solvent removal system thermocouples (13A) and (14A) respectively, and associated heating controllers (13) and (14) respectively. Said elements monitor and control of the temperatures in the associated invention system components.

Turning now to FIG. **2*a*, there is shown an expanded diagramatic view of a solvent removal system (8). Note in particular the inlet port (8*a*) at which solvent removal gas flow "A" is entered, and outlet port (8*b*) at which solvent vapor gas flow "A'" exits. While the solvent removal system (8) can be of any functional geometry, the preferred embodiment is a tube shapes containment of approximately one-half (0.5) inch in diameter, or less. (Note that said tube can be of a coiled, as shown in FIG. 15, or essentially straight, as shown in FIG. 2*a***, geometry and the claims, where appropiate, should be interpreted to include both such geometries or any functionally equivalent geometry). Said shape and size provides an effective volume flow rate therethrough when a typical one (1) liter per minute solvent vapor removal gas flow "A"-"A'" is entered thereto. It is preferred to cause solvent vapor removal gas flow "A"-"A'" to flow in the direction as shown because the relative solvent saturation of the gas in solvent vapor removal gas flow "A"-"A'" along its locus of flow, is closely matched to that of the solvent vapor inside the enclosed filter (7). However, solvent vapor removal gas flow could be caused to flow in a direction opposite, (e.g. "A'''"-"A"), to that shown and be within the scope of the present invention. It is emphasized that the temperature of said gas flow "A"-"A'''" or "A'''"-"A" is typically maintained at approximately one-hundred-fourty (140) degrees centigrade during use. No enclosed filter solvent removal system known to the inventors herein utilizes such a heated gas flow. Also shown in FIG. 2a are heater element (8h), nebulized sample particles flow (4PB) and connection means (12) to partially shown inductively coupled plasma or other sample analysis system (11). It is also mentioned that it is within the scope of the present invention to utilize a chemical dessicant or a dry gas in solvent vapor removal gas flow "A"-"A'''" or "A'''"-"A'''". FIG. 2b shows a crossectional view thereof take at a—a in FIG. 2a. Note that the enclosed filter (7) is demonstrated to be essentially tubular. This is considered to be an important aspect of the present invention.

It is also mentioned that while distinct elements are shown and described for performing various described functions in the present invention, it is within the scope of the present invention to perform more than one function in one element of the overall system of the present invention, or to combine various elements of the overall system into composite elements. For instance, desolvation chamber (6) and solvent removal system (8) might be combined into one system.

It will be appreciated, in view of the above, that the present invention provides a small internal volume enclosed filter (7) in which solvent vapor is filtered away from nebulized sample particles (4PB), the volume inside a one (1) to four (4) millmeter inner diameter GORE-TEX tube essentially comprising said enclosed filter volume. As a result, sample carry-over problems are minimized. In addition, the presently discussed embodiment of the present invention system (10), it is emphasized, does not require low temperatures to condense solvent vapor. Low temperatures can cause loss of nebulized sample particles (4PB) by way of recapture by condensing solvent vapor in systems which utilize condensers. Also, the present invention can be operated to provide high solvent removal efficiency by control of desolvation chamber (6) and solvent removal system (8) temperatures in conjunction with other system parameters, regardless of solvent type, (e.g. water, organic etc.). This is considered a very important point. The first embodiment of the present invention, thus, provides a sensitive, sample conserving, highly efficient system for providing highly nebulized sample particles and transporting them to a plasma or other analysis system.

Also shown in FIG. *2a* are thermocouple (14A) and heating control (14).

It is also to be understood that while the desolvation chamber (6) and solvent removal system (8) are each shown as being single units in the drawings, it is possible for each to be comprised of multiple sequential units.

Turning now to FIG. 4, there is shown a diagramatic view of a modified embodiment of the present ultrasonic nebulizer and enclosed filter solvent removal sample introduction invention (40). The discussion relating to FIGS. 1 and 3 is equally valid to point at which the mixture of solvent vapor and desolvated sample particles (4PB) enters the solvent removal system, except that no carrier gas (CG) is entered to the modified embodiment and inlet port (9) is not present. Note that FIG. 4, however, does show a low temperature condenser solvent removal system (48) with an enclosed filter (7) therethrough, and with heating elements (48H) present around the enclosed filter (7). Entering solvent vapor is maintained at a temperature above the boiling point of the solvent as it is transported through the enclosed filter, by said heating elements (48H), to the point along the enclosed filter at which it diffuses through the enclosed filter and into a low temperature condenser (48), in which the solvent vapor condenses and flows out of drain (48A), said flow being indicated by (4SU). Entering nebulized desolvated sample particles (4PB) are transported toward an analysis system (41) by way of connection means (49) from the solvent removal system, and connection means (49P) at the analysis system (41). Analysis system (41) is typically, when this modified embodiment of the present invention is used, a mass spectrometer which operates at a very low internal pressure, (e.g. ten-to-the-minus-fifth Torr). At connection means (49P) the pressure is typically approximately one (1) Tort. The pressure at the aerosol chamber (16) is typically 500 torr or greater. The driving force for the sample transport through the ultrasonic nebulization and enclosed filter sample preparation system (40) is thus identified. Turning now to FIG. 5, there is shown an expanded exemplary diagramatic view of the solvent removal system (48) in FIG. 4. Note that two sections (48A) and (48B) are shown. This is shown as an example only, and it is within the scope of the present invention to provide a solvent removal system with more or less than two sections, just as other elements of the present invention can be of other than exactly shown functional construction. Also shown in FIG. 5 are optional vacuum pumps (50) and low temperature maintaining liquid, typically liquid nitrogen or a mixture of dry ice and isopropanol (47). It is specifically noted that the modified embodiment of the present invention shown in FIGS. 4 and 5, can be termed a Universal Particle Beam Interface for use in interconnecting liquid chromatography and mass spectrometer systems. Connection means (49) can be a one-sixteenth (1/16) inch diameter tube, which will easily attach to most mass spectrometer systems without modification thereto.

It is also to be understood that the desolvation and solvent removal systems of the primary and modified embodiments of the present invention can be, in certain rare cases where desolvation of sample solution droplets is not desired, eliminated. The overall systems of FIGS. 1 and 4 depict such an additional embodiment of the present invention when the desolvation and solvent removal systems are visualized as inactive sample outlet means which can be connected to sample analysis systems (11) and (41). This would essentially be the case were the desolvation and solvent removal systems not operated during a sample preparation procedure.

Turning now to FIG. *6a*, there is shown one embodiment of the present direct injection micro nebulizer invention system (60), in cross sectional elevation as viewed from a position perpendicularly removed therefrom with the longitudinal dimension thereof projecting vertically upward from an underlying horizontal surface. In particular note that there is shown a primary body element (61), typically of unibody construction, a top element (62), a double nut element system (60A) comprised of upper nut (66) and lower nut (67), a sample delivery tube system (63) typically comprised of a sample delivery tube (*63b*) and a protective sleeve (*63a*), and an "O" ring (60R). FIG. 1b shows an enlarged view of a portion of the sample delivery tube system (63) in perspective, showing that the sample delivery tube system (63) can be comprised of a sample delivery tube (63b) and a protective sleeve (63a) through which the sample delivery tube (63b) is threaded, over at least a portion of its length. Said protective sleeve (63a) serves to protect the sample delivery tube (63b) against being crushed. (It is mentioned that a high strength crush resistant sample delivery tube (63b) per se could alone comprise a sample delivery tube system (63) with the protective sleeve (63a) being an integral component thereof, or a sample delivery tube per se could, alone, form the sample delivery tube system). It is also possible to provide sample delivery tube system (63) with a temperature control element such as an ohmic high resistance electrical conducting coil wound therearound along at least a portion of its length, (similar to the shown protective sleeve (63a)), so that during use of the direct injection micro nebulizer (60) in a sample analysis procedure the temperature of said sample delivery tube system (63) can be controlled. Controlling the temperature .thereof can lead to a decreased tendency of sample solids to adhere to and deposit inside the sample delivery tube (63b) during use. As a result a lessened chance that the sample delivery tube system (63) will become clogged is achieved. It is noted that the sample delivery tube (63b) is typically fifty (50) micrometers inner diameter and one-hundred-eighty (180) micrometers outer diameter. As well, the primary body element (1) is typically approximately one-hundred (100) milimeters in length. These dimensions are exemplary and not limiting, however.

Continuing, note that the top element (62), primary body element (61) and upper and lower nuts (66) and (67) respectively have centrally located longitudinally oriented holes therethrough, through which the sample delivery tube system (63), or at least the sample delivery tube (63b) per se can be threaded. (Note, the term "centrally located" is to be taken to mean that when the various elements of the present invention are properly attached to one another, the longitudinally oriented holes through them line up with one another so as to provide a continuous hole through the assembled direct injection micro nebulizer system). It is noted that the inner diameter of the centrally located longitudinally oriented hole through the top element (62) is typically, but not necessarily, two-hundred (200) micrometers. As a result the annular space between the outer surface of the sample delivery tube and the inner surface of the centrally located longitudinally oriented hole through the top element (62), when the sample delivery tube (63b) is threaded therethrough, is only approximately ten (10) micrometers radially. Also note that the primary body element (1) has, at its upper aspect, a first connection means (64), typically comprised of female screw threads, which first connection means interacts with complimentary connection means on the lower aspect of top element (62) to removably attach top element (62) to said primary body element (61). The primary body element (61) also provides a second connection means (65), at the lower aspect thereof, typically female screw threads, which second connection means (65) interact with complimentary connection means on the upper aspect of upper nut (66) of the double nut system (60A), to removably attach upper nut (66) to the lower aspect of the primary body element (61). The lower aspect of the upper nut (66) provides connection means (68), typically female screw threads, which connection means interact with complimentary connection means at the upper aspect of the lower nut (67) to removably attach said second nut (67) to said first nut (66). The primary body element also presents a third connection means (69), typically female screw threads, which allows attachment thereof to a source of gas flow, which gas flow is identified as "GD" in FIG. 7. Said third connection means (69) provides access to the centrally located space of the centrally located longitudinally oriented hole which is present through the primary body element (61), which space is designated (61S), by way of access port (69p).

Figures 6A, 7:
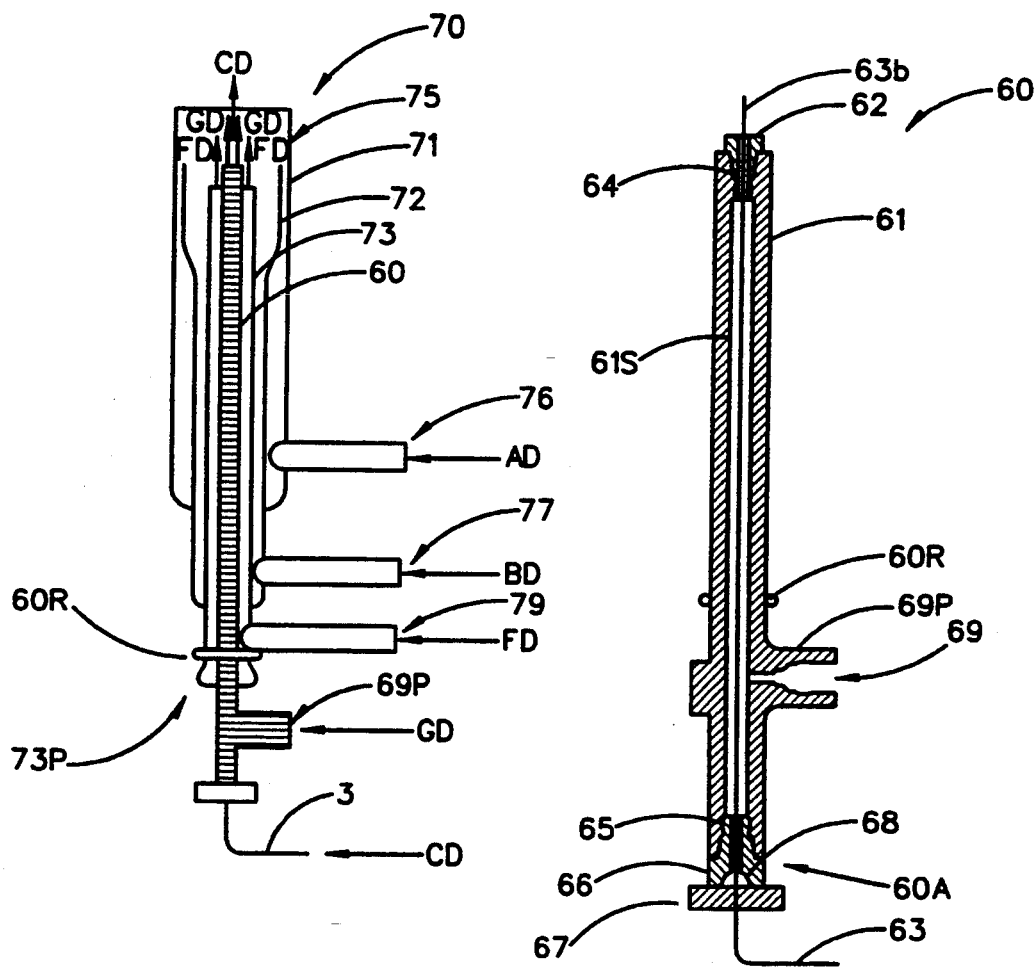
FIG. 6a shows a side elevational view of one embodiment of the present invention direct injection nebulizer in cross section, as viewed from a position perpendicularly removed therefrom.
FIG. 7 shows a side elevational view of a standard torch used in inductively coupled plasma analysis of samples, with the present invention present direct injection nebulizer in the sample injector tube thereof, viewed from a position perpendicularly removed therefrom.

It is to be understood that sample delivery tube system (63) is caused to be typically firmly, but removably, secured to the lower nut (67) of the double nut element system (60A). This is typically accomplished by providing a tapering female screw thread connection means at the lower aspect of the upper nut (66), into which complimentary connection means, comprising male screw threads at the upper aspect of the lower nut (67), can screw. As the complimentary connection means are caused to be screwed into the connection means (68) at the lower aspect of the upper nut (66), the centrally located hole through lower nut (67) is caused to collapse to some extent and firmly grasp said sample delivery tube system (63). It is also to be understood that the second connection means (65) at the lower aspect of the primary body element (61) allows complimentary connection means at the upper aspect of upper nut (66) to be manipulated with respect to the second connection means (65) on primary body element (61), so that the vertical location of the upper aspect of sample delivery tube (63b) can be precisely adjusted, when the sample delivery tube (63b) is threaded through the entire direct injection micro nebulizer system as shown in FIG. 6a. Said manipulation typically comprises turning of upper nut (66) with respect to primary body element (61), although any functionally equivalent system can be used. It is also noted that it is within the scope of the present invention to provide a sample delivery tube adjustment means in the form of a fixed retaining element at the second connection means (65) on primary body element (61). Said double nut system might be locked, (or the double nuts might be fused into a plug-like element, or replaced by a plug-like element), in a desired position at manufacture, or by a user during initial utilization, to form a fixed sample delivery tube adjustment means, (or retention), system. In addition, the second connection means might be a separate or integral plug in the primary body element, with a simple hole therein, through which simple hole the sample delivery tube is passed, and secured. The claims are to be interpreted to include such sample delivery tube adjustment means and retention systems under the terminology "sample delivery tube adjustment means". That is, the only "adjustment" possible might be during manufacture of the present invention, or by a single or a few initial actions by a user, or any functional equivalent thereto.

It should be also appreciated that the first connection means (64) at the top of primary body element (61) allows a user of the present invention to easily gain access to the upper aspect of the space (61S) within the primary body element (61) by removal of top element (62). This allows easy threading of sample delivery tube (63b), and easy cleaning of any sample solids which might accumulate within the space (61S) of the primary body element (61) during use in a sample analysis procedure. Said sample solids accumulation would, for instance, occur if the upper aspect of the sample delivery tube (63b) were not threaded through the longitudinally oriented centrally located hole in the top element. This would configure the system very much like the system shown in the Fassel et al. Patent drawings. It is noted, however, that the preferred arrangement of the present invention provides that the upper aspect of the sample delivery tube (63b) be threaded through the centrally located longitudinally oriented hole which transverses the top element (62).

The preferred materials from which the present invention is constructed are hydrofloric acid resistant and nonmetallic. This is important as some sample solids are solvated in solvent containing hydrofloric acid, and metals can interact with energy fields when the direct injection micro nebulizer is placed into an inductively coupled plasma analysis system, discussed below with respect to FIG. 7. Said interaction can cause untoward effects.

Turning now to FIG. 7, there is shown a side elevational view, as viewed from a position perpendicularly removed therefrom, of a vertically oriented standard torch (70) used with Inductively Coupled Plasma sample analysis systems. The present invention direct injection micro nebulizer (60) is shown placed therein. Note the presence of an outer tube (71), intermediate tube (72) and sample injector tube (73), as well as an outer port (76), intermediate port (77), auxiliary sample flow port (79) and a sample injector port (73p). When the standard torch (70) is used without the present invention (60) present therein, a nebulized sample flow is entered via the sample injector port (73p), and caused, typically under the influence of a pressure gradient, to flow vertically through the sample injector tube (73) and eject into the space above the vertically upper aspect of the sample injector tube, which space is designated as (75), at which location a plasma is typically caused to exist during use. Vertically or tangentially directed gas flows "AD" and "BD" are entered at the outer and intermediate ports (76) and (77) respectively, and under the influence of pressure gradients move upward through the spaces of the standard torch (70) into which they are injected. Typically tangentially directed flows are used in which the gas follows a vertically upward spiral-like motion. The purposes of said injected gas flows "AD" and "BD" are to shield the components of the standard torch (70), (e.g. (71), (72) and (73)), which they contact against the temperature and heat produced by a created plasma, and to aid the sample entry flow into said plasma. It is mentioned that normally the auxiliary sample flow port (79) will not be present when the standard torch (70) is used without the present invention (70) present therein.

Now, FIG. 7 shows the present invention (60) as inserted into the space within the sample injector tube (73) of the standard torch (70). In use the typically tangentially injected gas flows "AD" and "BD" at outer and intermediate ports (76) and (77) respectively will again be injected for purposes similar to those described above. With the present invention (60) present, however, a sample solution flow "CD" is entered into the sample delivery tube system (63) and caused to flow through the length of said sample delivery tube system (63), and eject from the vertically upper aspect thereof, (shown as sample delivery tube (63b) per se in the Figures), into the space (75) of the standard torch (70) in which a plasma can be created. Note it is also possible to induce sample flow by application of an electric potential between the upper and lower extents of the sample delivery tube, said voltage constituting a functionally equivalent pressure gradient. Such an interpretation is to be considered within the scope of the claims. Also note that the sample solution flow "CD" is not nebulized prior to entry to the sample delivery tube (6b). In addition, a gas flow "GD" is injected into port (69p) of the primary body element (61) and caused to flow through the annular space (61S) within the centrally located longitudinally oriented hole which vertically transverses the primary body element, between the outer surface of the sample delivery tube system (63) and the inner surface of the centrally located longitudinally oriented hole through the primary body element (61), and out thereof between the annular space between the outer surface of the sample delivery tube (63b) and the inner surface of the longitudinally oriented centrally located hole which is present through the top element (62). Interaction of the sample solution flow "CD" and the gas flow "GD" where both eject from the vertically upper aspect of the present invention causes nebulization of the sample solution to occur. Said nebulization can be aided by injection of an auxiliary sample gas flow "FD" at auxiliary sample port (79) of the standard torch (70), which gas flow "FD" ejects from the annular space between the outer surface of the primary body element (61) of the present invention and the inner surface of the sample injector tube (73) of the standard torch (70) and helps further nebulize, and to sweep, the nebulized sample flow created by interaction of flows "CD" and "GD" upward into space (75) of the standard torch (70).

Also note the presence of an "O" ring (60R) around the outer surface of primary body element (61). Said "O" ring (60R) serves to firmly secure the present invention (60) inside the sample injector tube of the standard torch (70).

Figures 6B, 8:
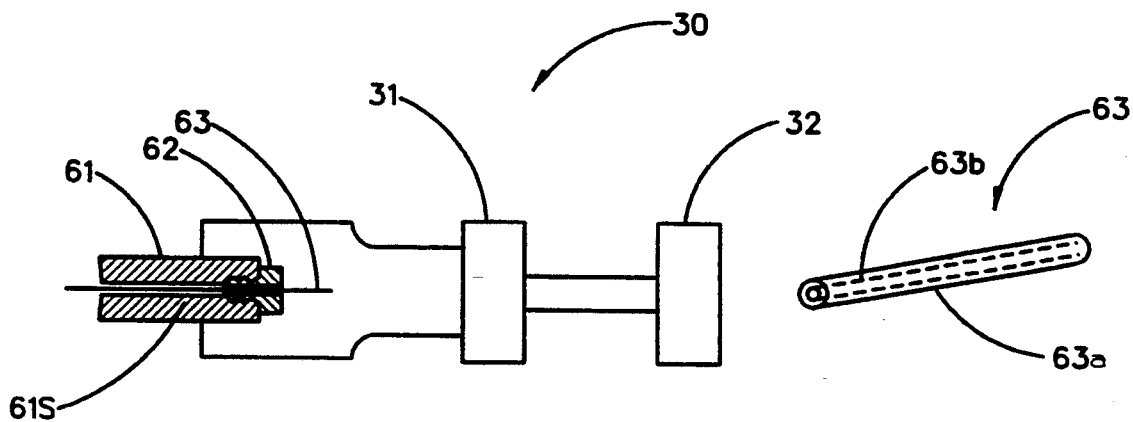
FIG. 6b shows a perspective view of a portion of a sample delivery tube system of the present direct injection micro nebulizer.
FIG. 8 shows a portion of the present direct injection micro nebulizer invention oriented horizontally in cross section, with block diagrams representing sample analysis system elements such as desolvation and solvent removal systems and sample analysis systems.
Figure 13:
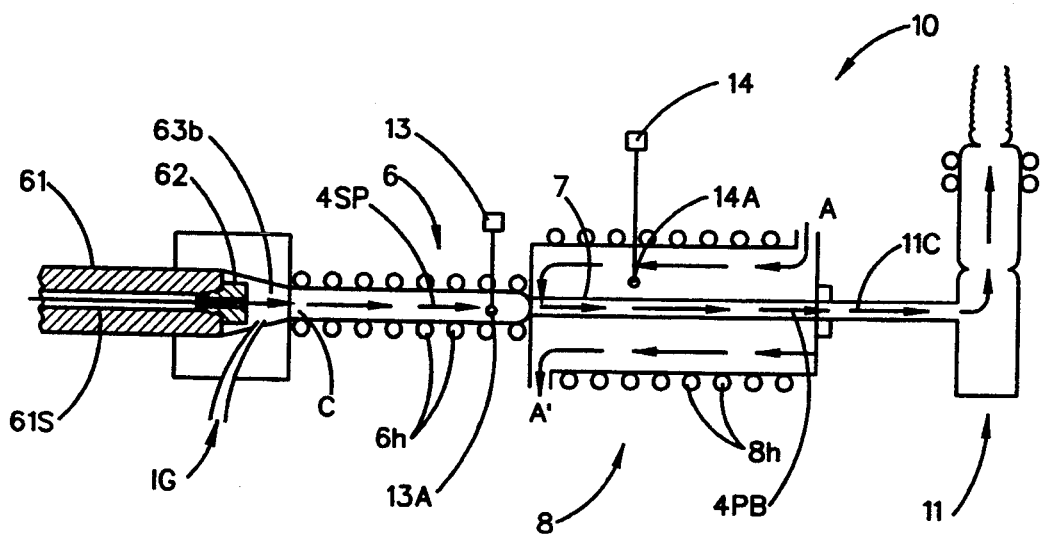
FIG. 13 shows the entire system of the primary embodiment of the present invention utilizing a direct injection micro nebulizer, in diagramatic form.
Figure 14:
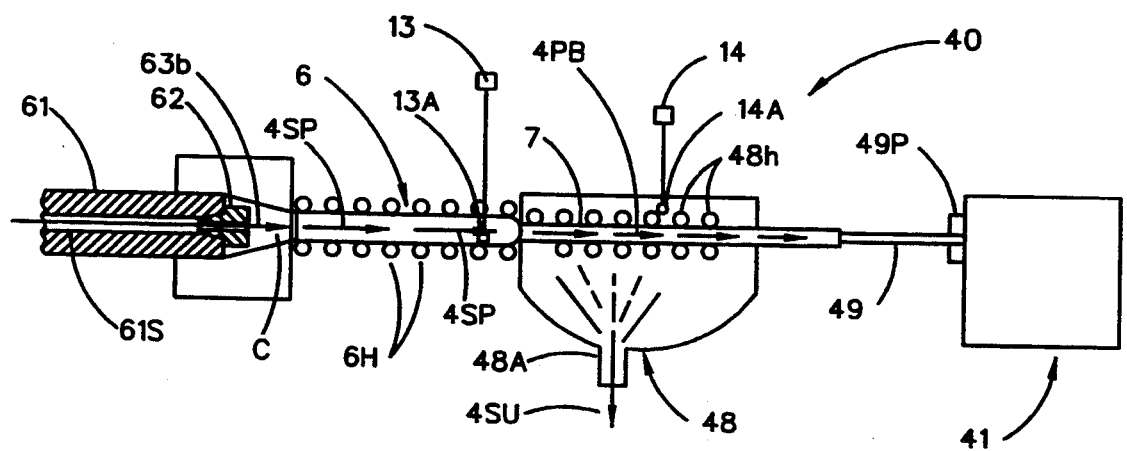
FIG. 14 shows the entire system of a modified embodiment of the present invention utilizing a direct injection micro nebulizer, in diagramatic form.

Turning now to FIG. 8, there is shown a partial view of the direct injection micro nebulizer (60), oriented with the longitudinal dimension thereof projecting horizontally so that top element (62) is at the right of the primary body element (61) in said figure. Also shown are blocks (31) and (32). Said blocks represent, generally, elements of sample analysis systems such as desolvation and solvent removal systems and mass spectrometers or any other analytical instruments including those which involve sample deposition and/or optical sample analysis methods. A particularly relevant interpretation of the block (31) would provide that it is the desolvation system (6) and/or the solvent removal systems (8) or (40) as described with respect to FIGS. 1, 2, 4 and 5. Such an interpretation effectively replaces the ultrasonic nebulizer system shown in FIGS. 1 and 4 with the direct injection micro nebulizer (60). FIGS. 13 and 14 diagramatically show said configuration. Note that the elements in FIGS. 13 and 14 are discussed elsewhere herein and said discussion is not repeated with respect to FIGS. 13 and 14. The present invention is then found in the combination of said enclosed filter solvent removal systems (8) or (40) with the disclosed ultrasonic or direct injection micro nebulizer systems. The claims are to be interpreted so as to include use of the combined enclosed filter solvent removal systems (8) and (40) with disclosed ultrasonic and direct injection micro nebulizer sample introduction systems, with any sample analysis system, (e.g. ICP torch system, mass spectrometer system etc. as represented by identification numeral (32) in FIG. 8). Also, it is to be understood that the direct injection micro nebulizer can be used in orientations wherein the longitudinal dimension of the direct injection micro nebulizer is other than vertical. The terms, "vertical", "upper", "top" etc., hence, are used herein only to facilitate disclosure and description.

Figures 12A, 12B:
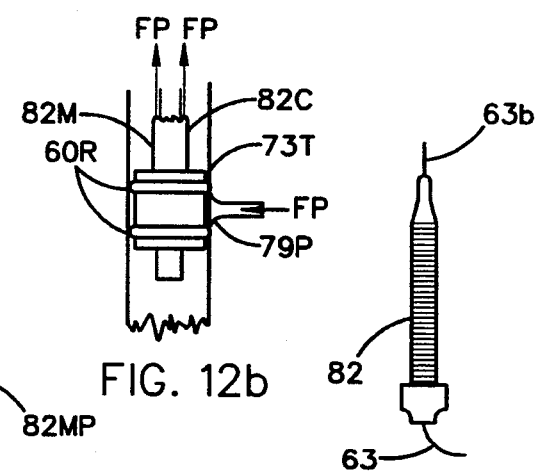
Figure 12C:
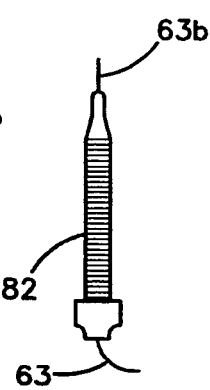
FIG. 12c shows a modified embodiement of a top element which includes a top element tip component. Said top element tip component provides high strength, is ultraviolet transparent, is not prone to heating when positioned near a plasma, provides tight tolerance inner diameter, and is less prone to being clogged by sample during use.

Finally, as regards FIGS. 6 and 7, the double nut element system (60A) of the present invention is a sample delivery tube system adjustment means and demonstrates one approach by which the vertical level of the upper aspect of the sample delivery tube system (63) can be easily and conveniently adjusted without the requirement that the present invention system be dismantled. Any functionally equivalent sample delivery tube system adjustment means, either repeatably adjustable or only adjustable at manufacture or one or a few times by a user etc., is to be considered as within the scope of the claims. In addition, either manual or automated adjustment of the sample delivery tube system position during use, are within the scope of the claims.

Turning now to FIGS. 9 and 10, there is shown a modified embodiment of the present direct injection micro nebulizer system and torch. FIG. 9 shows a direct injection micro nebulizer system (80) which is functionally similar to that described with respect to FIG. 6*a*, but with design modifications present. Generally, primary body element (81) provides first, second and third connection means (84), (85) and (89) respectively. Top element (82) attaches to first connection means (84) as does top element (62) attach to first connection means (64) in FIG. 6*a*, but top element (82) has present an elongated portion, (e.g. approximately seventy (70) milimeters long), which is not present in top element (62). In addition it is noted that the primary body element (81) is typically, but not necessarily, approximately one-hundred (100) milimeters long and approximately fifteen (15) milimeters outer diameter at the point at which it enters a torch as shown in FIG. 10. Reference to FIG. 10 shows that the elongated portion of top element (82) allows positioning sample delivery tube (63*b*) which threads therethrough near the location (95) in torch (90) where a plasma can be formed during use, without positioning the vertically upper aspect of primary body element (81) near thereto. Also shown in FIG. 9 are upper nut (86) and lower nut (87), the system of which allows easy adjustment of the vertical level of the upper aspect of the sample delivery tube (63*b*). Upper nut (86) attaches to second connection means (85) of the primary body element (81), and lower nut (87) attaches to the upper nut (86) by means of connection means (88). Sample delivery tube system (63) is firmly gripped by lower nut (87), and adjustment of the connection between the primary body element (81) and the upper nut (86) allows easy adjustment of the vertical level of the upper aspect of the sample delivery tube (63*b*). (Note that previously discussed fixed sample delivery tube system adjustment means might also be applied in the presently discussed embodiment). Third connection means (89) allows attachment to a source of gas flow shown as "GD" in FIG. 10. Interaction between sample flow "CD" and gas flow "GD" where both simultaneously eject from the upper aspect of top element (82) causes sample nebulization. Note that FIG. 10 shows a torch (90) which does not have a sample injector tube analogous to sample injector tube (73) in FIG. 7. As a result there is no provision for a gas flow analogous to gas flow "FG" shown in FIG. 7. The torch of FIG. 10 secures the primary body element (81) of the present invention within intermediate tube (92) by way of "O" rings (60R), which "O" rings are typically present as a pair thereof. The outer tube (91) is analogous to outer tube (71) of FIG. 7 and ports (96) and (97) are analogous to ports (76) and (77) in FIG. 7. Gas flows "AD" and "BD" are similar in both FIGS. 10 and 7. It is noted that when the torch (90) is used, it is possible to remove the direct injection micro nebulizer (80) therefrom and insert a separate sample injector tube assembly. FIG. 11 shows a modular sample injector tube system (80*p*) with substitute primary body element (81*p*) and sample injector tube (82*p*) present. This allows easy convertability of the torch from one which uses the present invention to one which allows use of sample nebulized by other (e.g. pneumatic, ultrasonic etc.) means at a distal location. The torch embodiment (90) of FIG. 10 is therefore termed a "demountable torch" which is suitable for use with a direct injection micro nebulizer system.

FIG. 10 shows lower nut (87), (or what could be a fixed position equivalent), as being coupled to a chromatography column (99). When this, or equivalent, configuration is present, a sample solution "CD" entered to the sample delivery tube (63*b*) will typically contain multi-analyte components. The chromatography column (99) will cause temporal separation of the various analyte components in a solution passed therethrough, based upon differing transport characteristics of each analyte component in the chromatography column. As a result, a single sample analysis procedure might be able to identify a sequence of sample analyte components very easily and conveniently. Chromatography, it is mentioned, is a well known technique for providing a means for separating sample analyte components in a multi component sample solution as said sample solution is passed through a chromatography column.

FIG. 12*a* shows, on an enlarged scale, a view of a modified top element (82*m*), which modified top element (82*m*) is similar to the top element (82) shown in FIG. 9, but has an additional top element circumscribing tube (82*c*) present. Said top element circumscribing tube (82*c*) serves to form an annular space surrounding the upper aspect of top element (82) through which annular space a gas of a desired temperature can be flowed during use, which flow of gas aids sample flow out of the sample delivery tube. Said gas flow being entered via modified top element port (82*mp*). Note that modified top element port (82*mp*) has "O" rings (60R) positioned with respect thereto so that they can form an encompassing seal when said modified top element (82*m*) is placed into, for instance, an ICP torch such as demonstrated in FIG. 7. FIG. 12*b* shows a partial view of a modified top element (82*m*) placed into a portion of an ICP torch tube (73*t*). Modified top element port (79*p*) allows entry of a gas flow "FP" which gas flow exits through the above identified annular space. (Note that gas flow "FP" and modified top element port (79*p*) serve somewhat analogous purposes to gas flow "FD" and auxiliary sample flow port (79) shown in FIG. 7 wherein a torch with a sample injector tube is represented). "O" rings (60R) are shown providing a seal between the modified top element (82*m*) and the ICP torch tube (73*t*) so that gas flow "FP", entered to port (79*p*), is directed into and through modified top element (82*m*) as shown. FIG. 12*c* shows yet another modification to a top element, (e.g. (82) or (82*m*)), in the form of an additional top element tip component (82s) at the uppermost extent thereof, as said top element is oriented in FIG. 12c. Note that sample delivery tube (63b) extends through the top element tip component (82s). Said top element tip component (82s) is typically tubular in shape and made of saphire or a functional equivalent. Said top element tip component (82s) is typically one (1) to ten (10) milimeters long and provides a tight tolerance inner diameter centrally oriented longitudinally directed hole therethrough. The purposes of the top element tip component (82s) include provision of a high strength, ultraviolet transparent, non-heat conducting component upon which sample is not prone to deposit and accumulate during use. During use top element (82) can be subject to abundant ultraviolet radiation by being placed near a plasma discharge. The presence of top element tip component (82s) helps to overcome adverse effects, such as invention clogging brought about by the effects of said ultraviolet radiation on the top element.

Figure 9:
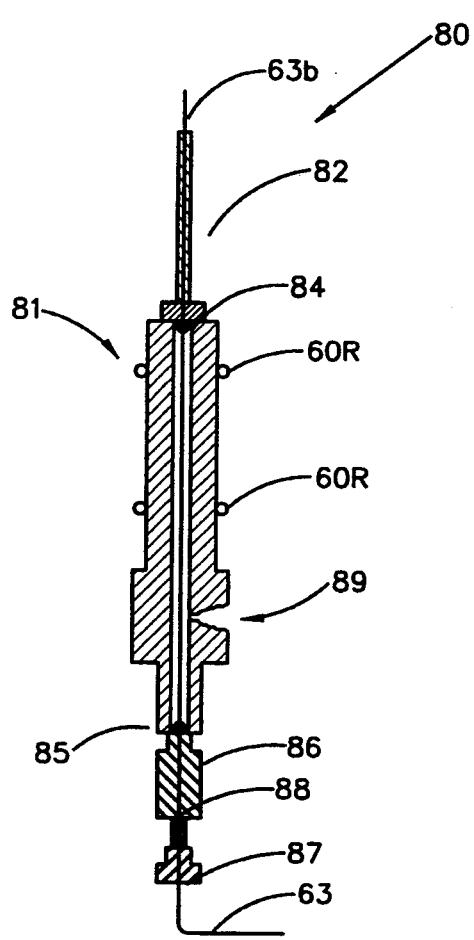
FIG. 9 shows a side elevational view of a modified embodiment of the present direct injection micro nebulizer invention in cross section, as viewed from a position perpendicularly removed therefrom.
Figure 10:
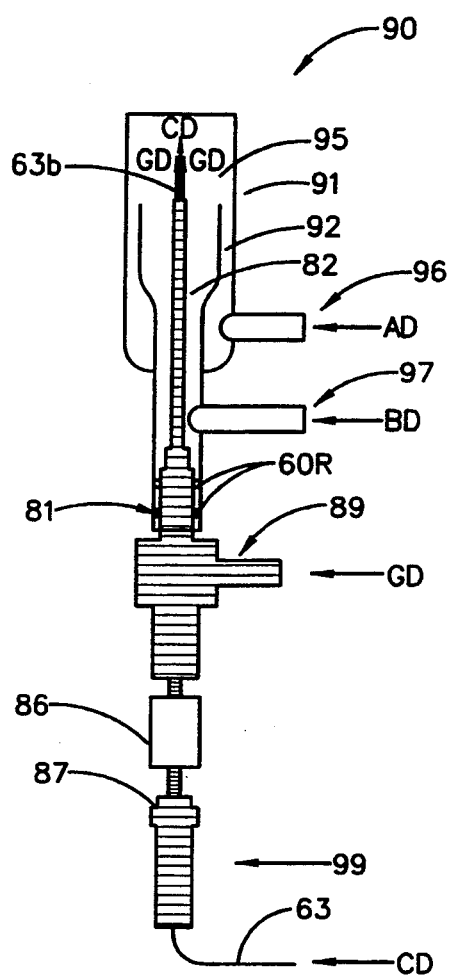
FIG. 10 shows a side elevational view of a specially designed torch used in inductively coupled plasma analysis of samples, with the modified embodiment of the present direct injection micro nebulizer invention present within the intermediate tube thereof, viewed from a position perpendicularly removed therefrom.
Figure 11:
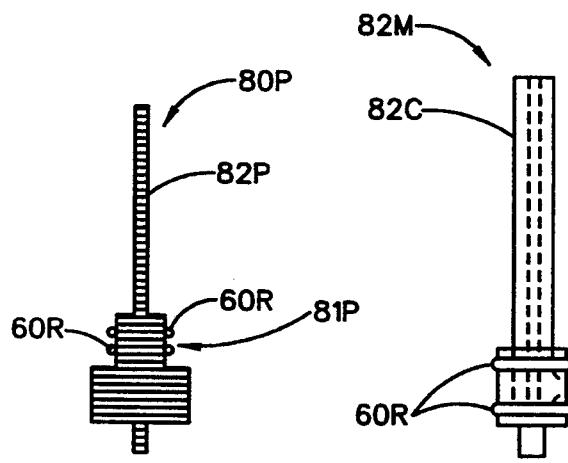
FIG. 11 shows a modular sample injector tube system which can be placed in the specially designed torch of FIG. 10 in place of the modified embodiment of the present direct injection micro nebulizer invention of FIG. 9 when it is desired to utilize sample solution nebulizing means located distally from the sample analysis system.

Turning now to FIGS. 13 and 14, there is shown a combination of the direct injection micro nebulizer (60) of FIG. 6a with the desolvation (6) system and solvent removal systems (8) and (48) of FIGS. 1 and 4 respectively. The discussion of the various elements and operation thereof in said FIGS. 13 and 14 presented previously is applicable and will not be repeated here. FIGS. 13 and 14 serve to provide a diagramatic reference of the system generally identified in FIG. 8. Note that FIG. 13 shows, in addition to elements discussed elsewhere herein, the presence of a gas (IG) entered so as to aid sample (C) flow into the desolvation system (6). This is approximately equivalent to gas flow "CG" shown in FIG. 1. It is to also be understood, though not directly shown in any Figure, that the direct injection micro nebulizer (80) of FIG. 9 can replace direct injection micro nebulizer (60) in FIGS. 13 and 14 and such an interpretation is to be considered within the scope of the claims.

It is to be understood that while inductively coupled plasma and mass spectrometers were used as examples herein, any gas phase or particle sample analysis system is to be considered equivalent for the purpose of claim interpretation.

It is also to be understood that sample solutions can originate from any source and can be subjected to component separation steps prior to being entered into a system for introducing samples as sample flows. This might be the case, for instance, where the sample solution is derived from a liquid chromatography source.

It must be emphasized that the direct injection micro nebulizer was defined herein with terminology appropriate when it is viewed with the longitudinal dimension thereof projecting vertically as shown in FIGS. 6, 7, 9, and 10. Terms such as "vertically", "top", "lower" and "upper" were used to describe elements and gas and sample flow directions etc. with reference to said Figures. To avoid confusion, the terms assigned elements of the direct injection micro nebulizer in discussion of FIGS. 6, 7, 9 and 10 were not changed when discussing the systems in FIGS. 8, 13 and 14. That is, for instance, "top element" was not redefined to be a "side element". As a result, claim language is to be read to include an interpretation of the words "vertical" and "upward" etc. as meaning "horizontal" and "sidewise" etc. when appropriate. Stated otherwise, the right side of the page upon which are present FIGS. 8, 13 and 14 should be considered to be the top therefore when necessary.

Figure 15:
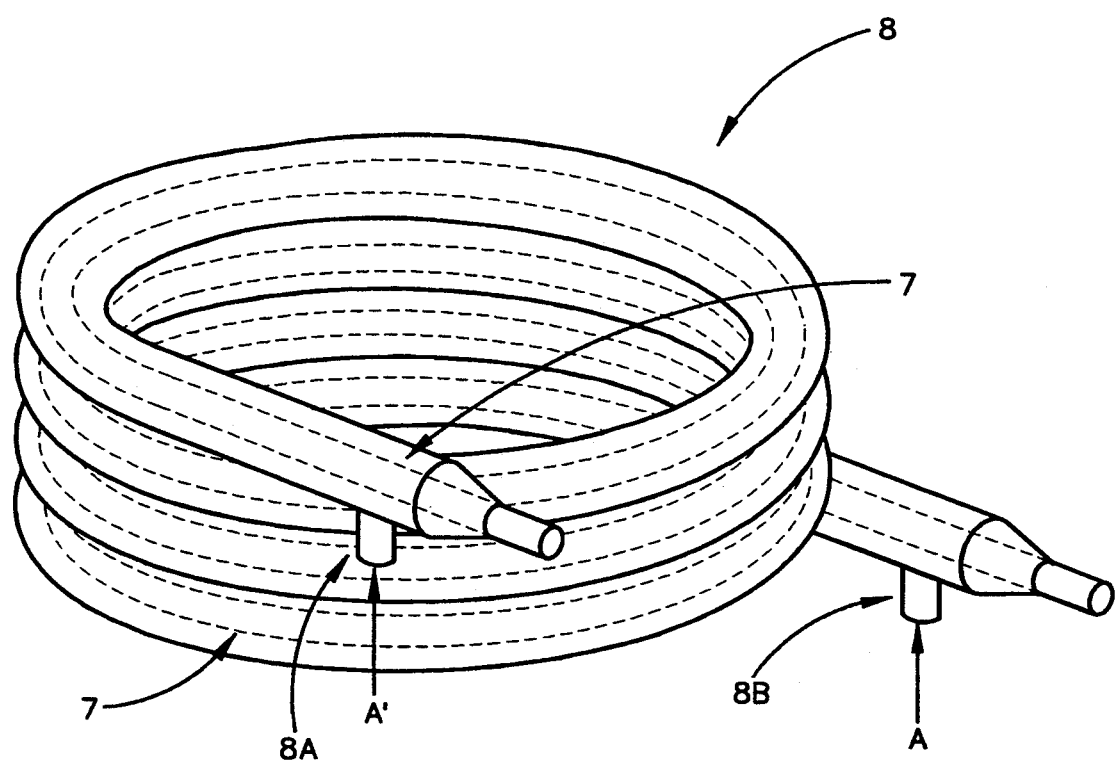
FIG. 15 shows the enclosed filter solvent removal system of the present invention configured as a coil.

Turning now to FIG. 15, there is shown a solvent removal system (8) with inlet port (8a) and outlet port (8b) for use in causing solvent vapor removal gas flow "A"-"A'" or "A'"-"A" over the outer surface of coiled essentially tubular shaped enclosed filter (7) therein during use. In use nebulized sample particles and solvent vapor are caused to flow into the inner volume of the coiled essentially tubular shaped enclosed filter (7). The nebulized sample particles are caused to diffuse through the walls system, and solvent vapor is caused to diffuse through the walls of said coiled essentially tubular shaped enclosed filter and be swept away by said solvent removal gas flow "A"-"A'" or "A'"-"A" as described elsewhere in this Specification with respect to solvent removal systems shown in an essentially straight configuration, (eq. see discussion regarding FIG. 1 for instance).

It is to be understood that while inductively coupled plasma and mass spectrometers were used as examples herein, any gas phase or particle sample analysis system is to be considered equivalent for the purpose of claim interpretation.

It is also to be understood that attachment between various nebulizer, desolvation, solvent removal and sample analysis systems can be direct or indirect. The claims are to be interpreted broadly enough to include the presence of intermediately positioned elements or systems when stating one system is attached to another.

It is also to be understood that sample solutions can originate from any source and can be subjected to component separation steps prior to being entered into a system for introducing samples as sample flows. This might be the case, for instance, where the sample solution is derived from a liquid chromatography source.

Having hereby disclosed the subject matter of this invention, it should be obvious that many modifications, substitutions, and variations of the present invention are possible in light of the teachings. It is therefore to be understood that the invention may be practiced other than as specifically described, and should be limited in breadth and scope only by the claims.

We claim:

1. A solvent removal system for removing solvent vapor from a mixture with desolvated nebulized sample particles prior to entering said desolvated nebulized sample particles into a sample analysis system which is attached to said solvent removal system at one extent thereof; said desolvated nebulized sample particles being formed by entering a sample solution to a nebulizer system and subjecting resulting nebulized sample solution droplets to a heating process in a desolvation chamber to which the solvent removal system is attached at an extent thereof removed from that at which the sample analysis system is attached; in which desolvation chamber are present heater means for causing the temperature therein to exceed the vaporization temperature of the solvent in said sample solution, which heater means heat solvent entered thereto above the vaporization temperature thereof during use; said solvent removal system being comprised of a coiled essentially tubular shaped enclosed filter encased within a containment such that a mixture of desolvated nebulized sample particles and vaporized solvent can be, during use, entered to space within said essentially tubular shaped enclosed filter, from the desolvation chamber, and caused to flow therethrough and into the sample analysis system wherein analysis thereof is performed, said coiled essentially tubular shaped enclosed filter being made from a material which allows said solvent vapor to diffuse therethrough, but which retains desolvated nebulized sample particles therewithin, said containment in which said enclosed filter is present providing means for removing said solvent vapor.

2. A solvent removal system as in claim 1, in which the desolvation chamber is a distinct separate element.

3. An solvent removal system as in claim 1, in which the desolvation chamber and solvent removal system are an integrated unit.

4. A solvent removal system as in claim 1, in which the coiled essentially tubular shaped enclosed filter is made from PTFE material.

5. A solvent removal system as in claim 4, in which the PTFE material has a porosity of at least seventy (70%) percent.

6. A solvent removal system as in claim 5, in which the PTFE material has a pore size of no greater than two (2) microns.

7. A solvent removal system as in claim 1, in which the coiled essentially tubular shaped enclosed filter has an inner diameter of approximately one (1) millimeters.

8. A solvent removal system as in claim 1, in which the coiled essentially tubular shaped enclosed filter has an inner diameter of approximately two (2) millimeters.

9. A solvent removal system as in claim 1, in which the essentially tubular shaped enclosed filter has in inner diameter of approximately four (4) millimeters.

10. A solvent removal system as in claim 1, in which the coiled essentially tubular shaped enclosed filter is approximately forty (40) centimeters in length.

11. A solvent removal system as in claim 1, in which the coiled essentially tubular shaped enclosed filter is essentially without turbulance creating bends therein.

12. A solvent removal system as in claim 1, in which a flow of gas over the coiled outer surface of the essentially tubular shaped enclosed filter is used to remove solvent vapor which diffuses through said essentially tubular shaped enclosed filter.

13. A solvent removal system as in claim 12, in which the gas in said flow of gas is heated, prior to being caused to flow over the coiled outer surface of the essentially tubular shped enclosed filter, to a temperature sufficient to prevent solvent vapor from condensing until removed from the vicinity of said coiled essentially tubular shaped enclosed filter.

14. A solvent removal system as in claim 1, in which the containment for the coiled essentially tubular shaped enclosed filter is essentially a low temperature condensor, which low temperature condensor serves to condense the solvent vapor which diffuses through said coiled essentially tubular shaped enclosed filter during use.

15. A solvent removal system as in claim 1, in which heating elements are present around the coiled essentially tubular shaped enclosed filter to maintain the temperature therein above that necessary to keep the solvent present therein vaporized.

16. A solvent removal system as in claim 1, which further comprises temperature sensors and automated temperature controllers present in the desolvation chamber and solvent removal system for use in maintaining temperatures in the desolvation chamber and solvent removal system at levels desired by a user thereof.

17. A solvant removal system as in claim 1, in which the nebulizer System is an ultrasonic nebulizer system.

18. A solvent removal system as in claim 17 in which the ultrasonic nebulizer comprises:
   a. an aerosol chamber;
   b. a piezoelectric crystal;
   c. a polyimide film;
   d. a structural heat sink;
   e. a sample outlet means;

which aerosol chamber comprises a means for allowing entry of a sample solution flow; means for connecting to the structural heat sink at one extent thereof and means for connecting to the sample outlet means at another extent thereof; which means for connecting to the structural heat sink is essentially tubular in shape with a constriction therein at some distance therealong; which polyimide film serves as an interface between the structural heat sink and the piezoelectric crystal; which structural heat sink with polyimide film and piezoelectric crystal on one extent thereof is connected to the aerosol chamber at the means for connection to said structural heat sink therein so that the piezoelectric crystal is sandwiched between the structural heat sink, polyimide film and the constriction in the aerosol chamber means for connecting to the structural heat sink so that no sample retaining crevasses are present at the point of connection; which piezoelectric crystal is, during use, caused to vibrate by application of electrical energy through an oscillator circuit of which it is an element; which piezoelectric crystal is buffered in its contact with the structural heat sink as it vibrates, by the polyimide film and which polyimide film also serves to reflect and focus vibrational energy produced to a position at which it can be better utilized in nebulizing sample solution; which structural heat sink, at an extent thereof distal to that at which the polyimide film and piezoelectric crystal are present, has present fins, which fins are subjected to a flow of cooling air during use, which cooling air serves to maintain the piezoelectric crystal at a desired temperature by way of heat conduction along the structural heat sink; through which means for allowing entry of a sample solution flow in the aerosol chamber a sample solution flow is entered during use; such that during use the entering sample solution flow is impinged in close proximity to the vibrating piezoelectric crystal whereat said sample solution is nebulized to form sample solution droplets by interaction with the vibrational energy produced by the vibrating piezoelectric crystal; which nebulized sample solution droplets can be transported into the sample outlet means to which the aerosol chamber is connected at the means for connection to the sample outlet means, said sample outlet means providing access to said solvent removal system.

19. A solvent removal system as in claim 18, in which the piezoelectric crystal vibrates at one-and-three-tenths (1.3) megahertz.

20. A solvant removal system as in claim 1, in which the nebulizer is a direct injection micro nebulizer system.

21. A solvent removal system as in claim 20 in which the direct injection micro nebulizer system comprises:
   a primary body element,
   a sample delivery tube system, and
   a sample delivery tube system adjustment means;
   said primary body, element being of a generally elongated shape presenting with a longitudinal dimension and having a first connection means at an upper aspect thereof, with upper aspect being defined as the vertically higher end of the primary body element as viewed in side elevation from a position perpendicularly removed therefrom while the longitudinal dimension thereof projects vertically upward and perpendicular to an underlying horizontal surface; and said primary body element also having a second connection means at a lower aspect thereof, and a third connection means thereon;

said sample delivery tube system comprising, a sample delivery tube;

said sample delivery tube system adjustment means being connected to said primary body element at the second connection means thereof;

said primary body element and sample delivery tube system adjustment means having centrally located longitudinally oriented holes therethrough;

said sample delivery tube system being threaded into the centrally located longitudinally oriented hole in the sample delivery tube system adjustment means and through the centrally located longitudinally oriented hole through the primary body element so that the upper aspect of the sample delivery tube is at a position near the upper aspect of the primary body element;

the position of the upper aspect of said sample delivery tube being precisely adjustable by manipulation of the sample delivery tube system adjustment means;

said sample delivery tube allowing a sample solution to be entered thereto at a lower aspect thereof and forced to flow through said sample delivery tube to the upper aspect thereof;

said third connection means on the primary body element allowing gas to be entered into and be forced to flow through the annular space formed between the outer surface of the sample delivery tube and the inner surface of the centrally located longitudinally oriented hole through the primary body element;

such that during use said sample solution flow and said gas flow are simultaneously ejected from the upper aspects of the sample delivery tube and the annular space between the outer surface of the sample delivery tube and the inner surface of the centrally located longitudinally oriented hole through the primary body element respectively, and interact with one another such that the sample solution is caused to be nebulized.

22. A solvent removal system as in claim 21, in which the direct injection micro nebulizer further comprises a top element having a centrally located longitudinally oriented hole therethrough, said top element being attached to the first connection means of the primary body element by way of complimentary connection means thereon, with said sample delivery tube being threaded through the centrally located longitudinally oriented hole in said top element so that the upper aspect thereof is positioned beyond the upper aspect of the top element, such that the gas which flows through the annular space between the outer surface of the sample delivery tube and the inner surface of the centrally located longitudinally oriented hole through the primary body element ejects from the annular space between the outer surface of the sample delivery tube and the inner surface of the centrally located longitudinally oriented hole through the top element during use.

23. A solvent removal system as in claim 21, in which the direct injection micro nebulizer system further comprises a protective sleeve along at least a portion of its length, to prevent crushing of said sample delivery tube.

24. A solvent removal system as in claim 21 in which the direct injection micro nebulizer system sample delivery tube system adjustment means comprises a double nut system, with the first nut thereof having connection means complimentary to the second connection means of the primary body element, and the second nut thereof having connection means thereon which are complimentary to additional connection means in the first nut thereof and means for firmly securing the sample delivery tube system such that when the two nuts are connected to one another, and the combination is connected to the primary body element at the second connection means thereof, adjustment of the first nut connection in the second connection means of the primary body element causes the position of the upper aspect of the sample delivery tube to be precisely adjusted with respect to the upper aspect of the primary body element.

25. A method of providing desolvated nebulized sample particles to a sample analysis system comprising the steps of:

a. obtaining a solvent removal system for removing solvent vapor from a mixture with desolvated nebulized sample particles prior to entering said desolvated nebulized sample particles into a sample analysis system, which sample analysis system is attached to said solvent removal system at one extent of said solvent removal system; said desolvated nebulized sample particles being formed by entering a sample solution to a nebulizer system and subjecting resulting nebulized sample solution droplets to a heating process in a desolvation chamber to which the solvent removal system is attached at an extent thereof removed from that at which the sample analysis system is attached; in which desolvation chamber are present heater means for causing the temperature therein to exceed the vaporization temperature of the solvent in said sample solution, which heater means heat solvent entered thereto above the vaporization temperature thereof during use; said solvent removal system being comprised of a coiled essentially tubular shaped enclosed filter encased within containment such that a mixture of desolvated nebulized sample particles and vaporized solvent can be, during use, entered to space within said essentially tubular shaped enclosed filter, from the desolvation chamber, and caused to flow therethrough and into the sample analysis system wherein analysis thereof is performed, said coiled essentially tubular shaped enclosed filter being made from a material which allows said solvent vapor to diffuse therethrough, but which retains desolvated nebulized sample particles therewithin, said containment in which said essentially tubular shaped enclosed filter is present providing means for removing said solvent vapor;

b. entering a sample solution to said nebulizer system;

c. causing resulting nebulized sample droplets to flow through said desolvation system to form a mixture of desolvated nebulized sample particles and vaporized solvent;

d. causing said mixture of desolvated nebulized sample particles and vaporized solvent to flow into the space within said coiled essentially tubular shaped enclosed filter in said solvent removal system such that said solvent vapor diffuses through the essentially tubular shaped enclosed filter, while said desolvated nebulized sample particles are caused to flow within the space within said essentially tubular shaped enclosed filter and into said sample analysts system for analysis therein.

26. A method of providing desolvated nebulized sample particles as in claim 25, which further comprises the step of flowing a gas over the coiled outer surface of the essentially tubular shaped enclosed filter to eliminate the solvent vapor which diffuses therethrough.

27. A method of providing desolvated nebulized sample particles as in claim 26 which further comprises the step of heating the gas which is flowed over the coiled outer surface of the essentially tubular shaped enclosed filter prior to causing it to so flow, such that it is of a temperature sufficiently high to prevent solvent vapor entering thereto from condensing prior to leaving the vicinity of the outer surface of said coiled essentially tubular shaped enclosed filter.

28. A method of providing desolvated nebulized sample particles as in claim 25, which further comprises the step of applying a low temperature environment beyond the outside surface of said coiled essentially tubular shaped enclosed filter to condense solvent vapor which diffuses through said coiled essentially tubular shaped enclosed filter.

29. A method of providing desolvated nebulized sample particles as in claim 25 which further comprises the step of applying heating means to the outer surface of said coiled essentially tubular shaped enclosed filter and causing said heating means to maintain said coiled essentially tubular shaped enclosed filter at a temperature sufficiently high to prevent solvent vapor from condensing inside thereof.

30. A combination desolvation chamber and solvent removal system for removing solvent vapor from a mixture with desolvated nebulized sample particles prior to entering said desolvated nebulized sample particles into a sample analysis system, which desolvation chamber is attached to said solvent removal system at one extent of said solvent removal system and which sample analysis system is attached thereto at another extent thereof; said desolvated nebulized sample particles being formed by entering a sample solution to a nebulizer system and subjecting resulting nebulized sample solution droplets to a heating process in said desolvation chamber; in which desolvation chamber are present heater means for causing the temperature therein to exceed the vaporization temperature of the solvent in said sample solution, which heater means heat solvent entered thereto above the vaporization temperature thereof during use; said solvent removal system being comprised of a coiled essentially tubular shaped enclosed filter encased within a containment such that a mixture of desolvated nebulized sample particles and vaporized solvent can be, during use, entered to space within said essentially tubular shaped enclosed filter, from the desolvation chamber, and caused to flow therethrough and into the sample analysis system wherein analysis thereof is performed, said coiled essentially tubular shaped enclosed filter being made from a material which allows said solvent vapor to diffuse therethrough, but which retains desolvated nebulized sample particles therewithin for transport to said sample analysis system; said coiled essentially tubular shaped enclosed filter being encompassed by heating elements for maintaining the temperature inside thereof above the vaporization temperature of said solvent during use, and said coiled containment in which said essentially tubular shaped enclosed filter is present providing means for removing said coiled solvent vapor.

31. A combination desolvation chamber and solvent removal system as in claim 30, in which the coiled essentially tubular shaped enclosed filter is made from PTFE material with a pore size of no greater than two (2) microns and a porosity of at least seventy (70%) percent, and which is approximately forty (40) centimeters long.

32. A combination desolvation chamber and solvent removal system as in claim 30, in which a flow of heated gas over the outer surface of said coiled essentially tubular shaped enclosed filter is used to remove said solvent vapor which diffuses through said coiled essentially tubular shaped enclosed filter from the vicinity thereof during use.

33. A combination desolvation chamber and solvent removal system as in claim 30, in which the containment for the coiled essentially tubular shaped enclosed filter is essentially a low temperature condenser, which low temperature condenser serves to condense the solvent vapor which diffuses through said coiled essentially tubular shaped enclosed filter and remove it from the vicinity thereof during use.

34. A combination nebulizer, desolvation chamber and solvent removal system for producing nebulized sample solution droplets, desolvating them to produce desolvated nebulized sample particles and removing the resulting solvent vapor from a mixture with said desolvated nebulized sample particles prior to entering said desolvated nebulized sample particles into a sample analysis system; which desolvation chamber is attached to said solvent removal system at one extent of said solvent removal system and which sample analysis system is attached thereto at another extent thereof; said desolvated nebulized sample particles being formed by entering a sample solution to said nebulizer system and subjecting the resulting nebulized sample solution droplets to a heating process in said desolvation chamber; in which desolvation chamber are present heater means for causing the temperature therein to exceed the vaporization temperature of the solvent in said sample solution, which heater means heat solvent entered thereto above the vaporization temperature thereof during use; said solvent removal system being comprised of a coiled an essentially tubular shaped enclosed filter encased within a containment such that a mixture of desolvated nebulized sample particles and vaporized solvent can be, during use, entered to space within said coiled essentially tubular shaped enclosed filter, from the desolvation chamber, and caused to flow therethrough and into the sample analysis system wherein analysis thereof is performed, said coiled essentially tubular shaped enclosed filter being made from a material which allows said solvent vapor to diffuse therethrough, but which retains desolvated nebulized sample particles therewithin for transport to said sample analysis system; said coiled essentially tubular shaped enclosed filter being ecompassed by heating elements for maintaining the temperature therein above the vaporization temperature of said solvent during use, and said containment in which said coiled essentially tubular shaped enclosed filter is present providing means for removing said solvent vapor.

35. A combination nebulizer, desolvation chamber and solvent removal system as in claim 34, in which the coiled essentially tubular shaped enclosed filter is made from PTFE material with a pore size of no greater than two (2) microns, a porosity of at least seventy (70%) percent, and which is approximately forty (40) centimeters long.

36. A combination nebulizer, desolvation chamber and solvent removal system as in claim 34, in which a flow of heated gas over the outer surface of said coiled essentially tubular shaped enclosed filter is used to remove said solvent vapor which diffuses through said coiled essentially tubular shaped enclosed filter and remove it from the vicinity thereof during use.

37. A combination nebulizer, desolvation chamber and solvent removal system as in claim 34, in which the containment for the coiled essentially tubular shaped enclosed filter is essentially a low temperature condenser, which low temperature condenser serves to condense the solvent vapor which diffuses through said coiled essentially tubular shaped enclosed filter and remove it from the vicinity thereof during use.

38. A combination nebulizer, desolvation and solvent removal system as in claim 34, in which the nebulizer is an ultrasonic nebulizer system.

39. A combination nebulizer, desolvation and solvent removal system as in claim 34 in which the nebulizer is a direct injection micro nebulizer system.

* * * * *